(12) United States Patent
Emken et al.

(10) Patent No.: US 11,109,779 B2
(45) Date of Patent: *Sep. 7, 2021

(54) CHEMICAL MODIFICATION OF ANALYTE PERMEABLE MEMBRANE FOR ENHANCED OXIDATIVE STABILITY

(71) Applicant: Senseonics, Incorporated, Germantown, MD (US)

(72) Inventors: Jeremy Emken, Germantown, MD (US); Philip Huffstetler, Germantown, MD (US); Todd Whitehurst, Germantown, MD (US); Masika Hinds, Germantown, MD (US); Mark Mortellaro, Germantown, MD (US); Abhi Chavan, Germantown, MD (US); Bryan Hays, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 482 days.

This patent is subject to a terminal disclaimer.

(21) Appl. No.: 16/009,963

(22) Filed: Jun. 15, 2018

(65) Prior Publication Data
US 2018/0353113 A1 Dec. 13, 2018

Related U.S. Application Data

(63) Continuation-in-part of application No. 15/250,087, filed on Aug. 29, 2016, now Pat. No. 10,064,573, (Continued)

(51) Int. Cl.
*A61B 5/1455* (2006.01)
*A61B 5/1495* (2006.01)
(Continued)

(52) U.S. Cl.
CPC ........ *A61B 5/14532* (2013.01); *A61B 5/1459* (2013.01); *A61B 5/0031* (2013.01);
(Continued)

(58) Field of Classification Search
CPC . A61B 5/1455; A61B 5/1459; A61B 5/14532; A61B 5/6867
See application file for complete search history.

(56) References Cited

U.S. PATENT DOCUMENTS 4,925,268 A   5/1990  Iyer et al.
5,262,305 A * 11/1993  Heller .................... C12Q 1/002
                                                        204/403.1
(Continued)

FOREIGN PATENT DOCUMENTS

CN    1658902 A    8/2005
CN    1942764 A    4/2007
(Continued)

*Primary Examiner* — Eric F Winakur
(74) *Attorney, Agent, or Firm* — Rothwell, Figg, Ernst & Manbeck, P.C.

(57) ABSTRACT

A sensor that may be used to detect the presence, amount, and/or concentration of an analyte in a medium within an animal. The sensor may include a sensor housing, an indicator element embedded within and/or covering at least a portion of the sensor housing, and a membrane over the indicator element. The sensor may include one or more of a first coating on an inner surface of the membrane, a second coating on an outer surface of the membrane, and a layer on the outside of the indicator element. One or more of the first coating, second coating, and layer may reduce deterioration of the indicator element by catalyzing degradation of reactive oxygen species (ROS). The one or more coatings on the membrane may increase the light blocking capability of the membrane, which may improve the accuracy of the sensor.

20 Claims, 19 Drawing Sheets

Related U.S. Application Data which is a continuation of application No. 14/142,017, filed on Dec. 27, 2013, now Pat. No. 9,427,182.

(60) Provisional application No. 61/746,790, filed on Dec. 28, 2012, provisional application No. 61/847,881, filed on Jul. 18, 2013, provisional application No. 62/520,784, filed on Jun. 16, 2017.

(51) Int. Cl.
- *A61B 5/145* (2006.01)
- *A61B 5/1459* (2006.01)
- *A61B 5/00* (2006.01)

(52) U.S. Cl.
CPC ............. *A61B 5/1451* (2013.01); *A61B 5/746* (2013.01); *A61B 2560/0219* (2013.01); *A61B 2562/162* (2013.01); *A61B 2562/18* (2013.01); *A61B 2562/185* (2013.01)

(56) References Cited

U.S. PATENT DOCUMENTS

| | | |
|---|---|---|
| 6,330,464 B1 | 12/2001 | Colvin, Jr. et al. |
| 6,344,630 B1 | 2/2002 | Jarvis et al. |
| 6,405,066 B1 | 6/2002 | Essenpreis et al. |
| 6,702,857 B2 | 3/2004 | Brauker et al. |
| 7,713,745 B2 | 5/2010 | Colvin, Jr. et al. |
| 7,800,078 B2 | 9/2010 | Colvin, Jr. et al. |
| 7,901,354 B2 | 3/2011 | Shults et al. |
| 8,126,554 B2 | 2/2012 | Kane et al. |
| 8,657,745 B2 | 2/2014 | Brauker et al. |
| 8,940,544 B2 | 1/2015 | Suri et al. |
| 9,339,222 B2 | 5/2016 | Simpson et al. |
| 9,414,775 B2 | 8/2016 | Colvin, Jr. et al. |
| 9,797,909 B2 | 10/2017 | Paterson et al. |
| 9,931,067 B2 | 4/2018 | Shults et al. |
| 9,970,940 B2 | 5/2018 | Crane et al. |
| 2004/0063167 A1* | 4/2004 | Kaastrup ................ C12Q 1/006 435/27 |
| 2004/0176672 A1 | 9/2004 | Silver et al. |
| 2005/0031689 A1 | 2/2005 | Shults et al. |
| 2005/0175702 A1 | 8/2005 | Muller-Schulte |
| 2005/0215871 A1* | 9/2005 | Feldman ............ A61B 5/14532 600/309 |
| 2007/0235331 A1 | 10/2007 | Simpson et al. |
| 2009/0124875 A1 | 5/2009 | Bentsen et al. |
| 2010/0123972 A1 | 5/2010 | Higashino |
| 2011/0236989 A1 | 9/2011 | Suri et al. |
| 2012/0238842 A1 | 9/2012 | Colvin, Jr. et al. |
| 2013/0241745 A1 | 9/2013 | Colvin, Jr. et al. |

FOREIGN PATENT DOCUMENTS

| | | |
|---|---|---|
| WO | 2010/119916 A1 | 10/2010 |
| WO | 2010/123972 A1 | 10/2010 |
| WO | 2014/043204 A1 | 3/2014 |

* cited by examiner

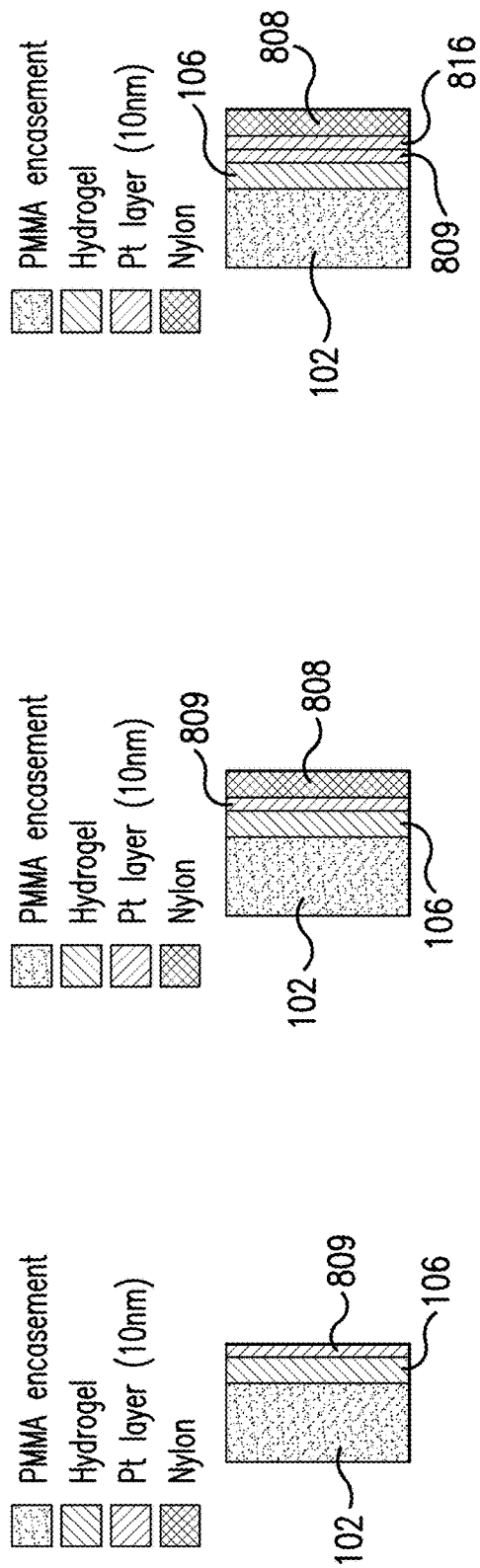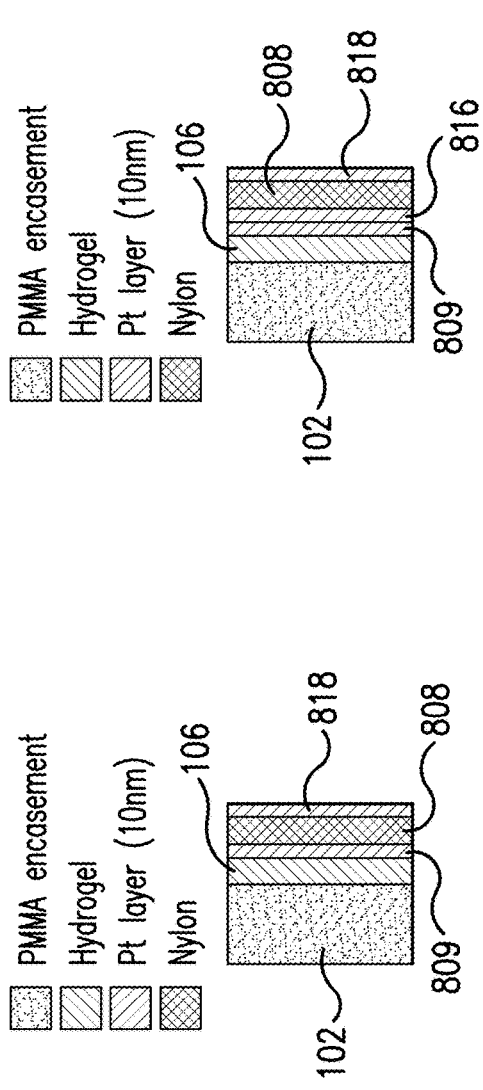

CHEMICAL MODIFICATION OF ANALYTE PERMEABLE MEMBRANE FOR ENHANCED OXIDATIVE STABILITY

CROSS-REFERENCE TO RELATED APPLICATION

The present application is a continuation-in-part of U.S. patent application Ser. No. 15/250,087, filed on Aug. 29, 2016, which is a continuation of U.S. patent application Ser. No. 14/142,017, filed on Dec. 27, 2013, now U.S. Pat. No. 9,427,182, which claims the benefit of priority to U.S. Provisional Application Ser. No. 61/746,790, filed on Dec. 28, 2012, and U.S. Provisional Application Ser. No. 61/847,881, filed on Jul. 18, 2013, all of which are incorporated herein by reference in their entireties. The present application also claims the benefit of priority to U.S. Provisional Application Ser. No. 62/520,784, filed on Jun. 16, 2017, which is incorporated herein by reference in its entirety.

BACKGROUND

Field of Invention

The present invention relates generally to sensors for implantation or insertion within a living animal and measurement of an analyte in a medium within the living animal. Specifically, the present invention relates to sensors having a membrane over an indicator element on the surface of the sensor body.

Discussion of the Background

A sensor may include an indicator element, such as, for example, indicator molecules embedded or polymerized in or onto a polymer graft (i.e., layer or matrix). For example, in an implantable fluorescence-based glucose sensor, fluorescent indicator molecules may reversibly bind glucose and, when illuminated with excitation light (e.g., light having a wavelength of approximately 378 nm), emit an amount of light (e.g., light in the range of 400 to 500 nm) that depends on whether glucose is bound to the indicator molecule.

If a sensor is implanted in the body of a living animal, the animal's immune system begins to attack the sensor. For instance, if a sensor is implanted in a human, white blood cells attack the sensor as a foreign body, and, in the initial immune system onslaught, neutrophils are the primary white blood cells attacking the sensor. Macrophages and giant cells may further attack the sensor. The defense mechanism of neutrophils and other white blood cells includes the release of highly oxidative substances known as reactive oxygen species (ROS), such as hydrogen peroxide ($H_2O_2$), hydroxyl radical (OH.), hypochlorite ($OCl^-$), peroxynitrite ($OONO^-$), and superoxide ($O_2^-$).

ROS, such as hydrogen peroxide, may degrade indicator molecules. For instance, in indicator molecules having a boronate group, hydrogen peroxide may degrade the indicator molecules by oxidizing the boronate group, thus disabling the ability of the indicator molecule to bind glucose.

In addition, if the sensor is an optical sensor, light (e.g., excitation light, fluorescent light emitted by the indicator molecules) from the sensor may pass through the indicator element or other transparent portions of the sensor. If the sensor has been implanted in animal tissue, the light may be reflected by the tissue or may cause the tissue to fluoresce and return light at a different wavelength. The reflected and fluoresced light from the tissue may return through the indicator element or other transparent part of the sensor and may be received by one or more light detectors (e.g., photodiodes) of the sensor. This results in noise in the signals received by the light detectors.

Moreover, if the animal (e.g., a human patient) is in a brightly lit area, then the light may pass through the patient's skin and be received by the light detectors of the sensor. This could also introduce noise into the signals received by the light detectors. Thus, erroneous sensor readings may occur because light detectors in an implanted sensor may receive additional signals unrelated to the analyte concentration.

There is presently a need in the art for improvements in optical sensor isolation and reducing indicator element degradation.

SUMMARY

The present invention overcomes the disadvantages of prior systems by providing, among other advantages, improved optical isolation and/or reduced indicator element degradation while still allowing an analyte of interest to reach the indicator element.

One aspect of the present invention may provide a sensor including a sensor housing, an indicator element, a membrane, a coating, and a layer. The indicator element may be embedded within and/or covering at least a portion of the sensor housing. The membrane may be over at least a portion of the indicator element, and the membrane may include an inner surface and an outer surface. The coating may be on one of the inner and outer surfaces of the membrane, and the coating may reduce deterioration of the indicator element by catalyzing degradation of reactive oxygen species (ROS). The layer may be on the outside of the indicator element. The layer may be between the indicator element and the membrane. The layer may reduce deterioration of the indicator element by catalyzing degradation of ROS.

In some embodiments, the coating may be on the outer surface of the membrane. In some embodiments, the coating may be on the inner surface of the membrane, and the layer may be between the indicator element and the coating on the inner surface of the membrane. In some embodiments, the coating may be a first coating, the sensor may further include a second coating on the outer surface of the membrane, and the second coating may reduce deterioration of the indicator element by catalyzing degradation of ROS. In some embodiments, the first and second coatings may be sputter coatings. In some embodiments, the first and second coatings may include platinum.

In some embodiments, the coating may be a sputter coating. In some embodiments, the coating may include platinum. In some embodiments, the layer may include platinum. In some embodiments, the layer may be sputtered on the outside of the indicator element. In some embodiments, the membrane with the coating on one of the inner and outer surfaces of the membrane may be opaque.

In some embodiments, the membrane may be attached to the sensor housing. In some embodiments, the membrane may be attached to the sensor housing by heat bonding or with a biocompatible adhesive. In some embodiments, the membrane may be attached to the sensor housing using laser bonding. In some embodiments, the membrane may be a mesh material.

In some embodiments, the membrane may have pores configured to substantially prevent white blood cells from passing through the membrane but to permit the analyte to pass through the membrane. In some embodiments, the analyte may be glucose. In some embodiments, the membrane may be wrapped around the indicator element. In some embodiments, the indicator element may be a polymer graft including indicator molecules. In some embodiments, one or more of the membrane and the coating may be configured to block (i) external light from reaching the indicator element and (ii) light from the sensor housing that has passed through the indicator element from reaching the bodily tissue of the living animal.

Another aspect of the present invention may provide a method of attaching a membrane to a sensor housing. The method may include irradiating the membrane with laser light, and at least an inner surface of the membrane may be coated with a material configured to absorb the laser light and melt. The method may include the material absorbing the laser light and bonding the membrane to the sensor housing.

In some embodiments, the material may be configured to catalyze degradation of reactive oxygen species (ROS). In some embodiments, one or more of the sensor housing and the membrane may not absorb the laser light. In some embodiments, the sensor housing and the membrane may not absorb the laser light. In some embodiments, the laser light may be infrared light. In some embodiments, one or more of the sensor housing and the membrane may absorb the laser light.

Yet another aspect of the present invention may provide a sensor including a sensor housing, an indicator element, a membrane, a coating, and a layer. The indicator element may be embedded within and/or covering at least a portion of the sensor housing. The membrane may be over at least a portion of the indicator element, and the membrane may include an inner surface and an outer surface. The coating may be on one of the inner and outer surfaces of the membrane. One or more of the membrane and the coating may be configured to block (i) external light from reaching the indicator element and (ii) light from the sensor housing that has passed through the indicator element from reaching the bodily tissue of the living animal. The layer may be on the outside of the indicator element. The layer may be between the indicator element and the membrane. The layer may be configured to block (i) external light from reaching the indicator element and (ii) light from the sensor housing that has passed through the indicator element from reaching the bodily tissue of the living animal.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIGS. 17A-17E illustrate non-limiting examples of sensors embodying aspects of the present invention.

DETAILED DESCRIPTION OF PREFERRED EMBODIMENTS

Figure 1:
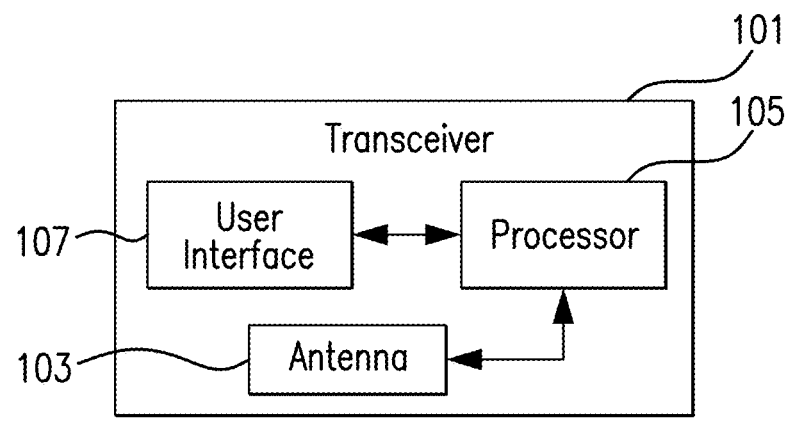
FIG. 1 is a schematic view of a sensor system, which includes an implantable sensor and a sensor reader, embodying aspects of the present invention.
Figure 1:
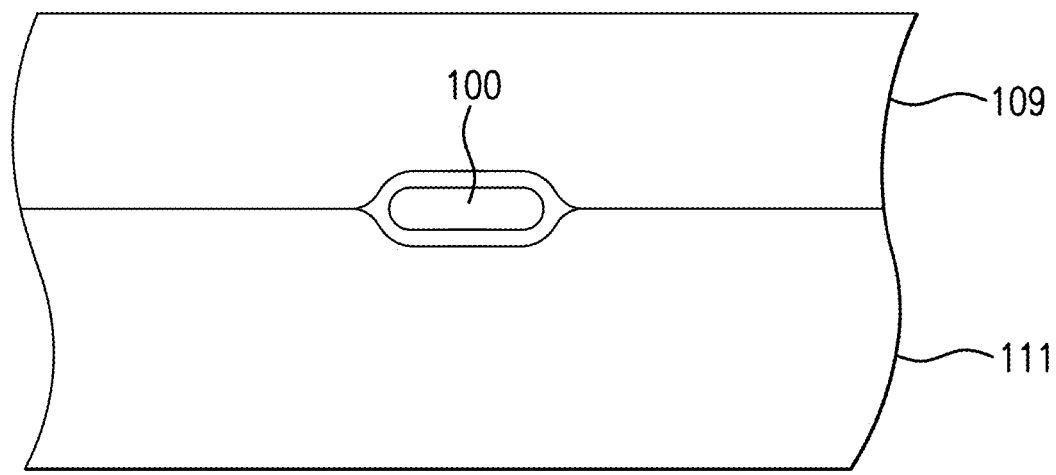
Figure 2:
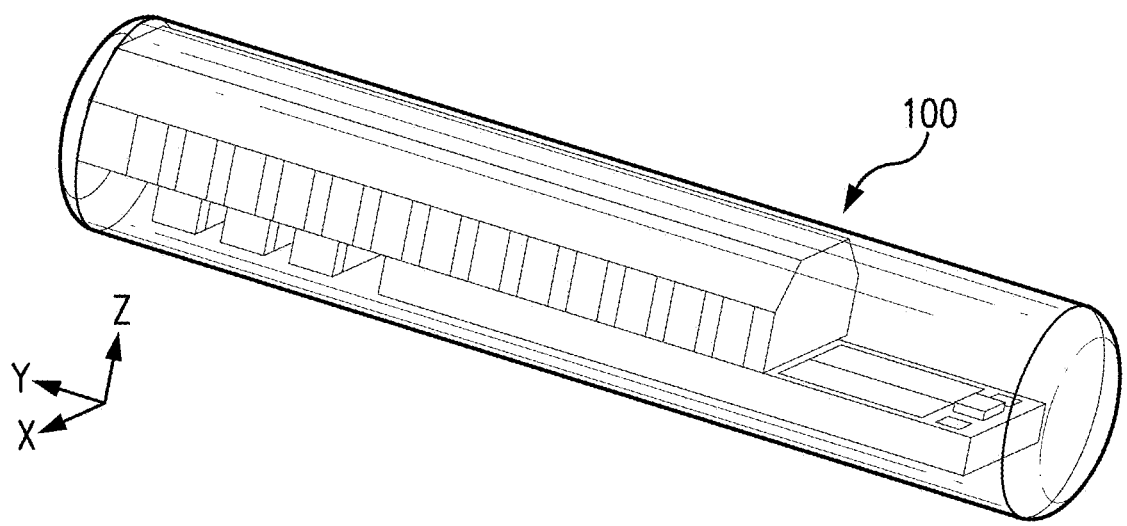
FIG. 2 illustrates a perspective view of a sensor embodying aspects of the present invention.

FIG. 1 is a schematic view of a sensor system embodying aspects of the present invention. In some embodiments, the system includes a sensor 100 and an external transceiver 101. In some embodiments, as shown in FIG. 1, the sensor 100 may be implanted in a living animal (e.g., a living human). The sensor 100 may be implanted, for example, in a living animal's arm, wrist, leg, abdomen, or other region of the living animal suitable for sensor implantation. For example, as shown in FIG. 1, in one non-limiting embodiment, the sensor 100 may be implanted between the skin 109 and subcutaneous tissues 111. In some embodiments, the sensor 100 may be a fully implantable sensor. However, this is not required, and, in some alternative embodiments, the sensor 100 may be a partially implantable (e.g., transcutaneous) sensor. In some embodiments, the sensor 100 may measure an amount or concentration of an analyte (e.g., glucose) in a medium (e.g., interstitial fluid) of the living animal. In some embodiments, the sensor 100 may be an optical sensor. In some alternative embodiments, the sensor 100 may be a chemical or biochemical sensor.

In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive one or more measurements (e.g., analyte measurements and/or temperature measurements) from the sensor (e.g., via near field communication (NFC)). However, this is not required, and, in some alternative embodiments, the transceiver 101 may power and/or communicate with the sensing system 105 via one or more wired connections. In some non-limiting embodiments, the transceiver 101 may be a smartphone (e.g., an NFC-enabled smartphone). In some embodiments, the transceiver 101 may communicate information (e.g., one or more analyte measurements) wirelessly (e.g., via a Bluetooth™ communication standard such as, for example and without limitation Bluetooth Low Energy) to a hand held application running on a display device (e.g., smartphone).

In some embodiments, the transceiver 101 may include one or more of an antenna 103, a processor 105, and a user interface 107. In some non-limiting embodiments, the user interface 107 may include a liquid crystal display (LCD), but, in other embodiments, different types of displays may be used.

In some embodiments, the antenna 103 may include an inductive element, such as, for example, a coil. The antenna 103 may generate an electromagnetic wave or electrodynamic field (e.g., by using a coil) to induce a current in an inductive element (e.g., inductive element 114 of FIGS. 3-8) of the sensor 100, which may power the sensor 100. The antenna 103 may also convey data (e.g., commands) to the sensor 100. For example, in some non-limiting embodiments, the antenna 103 may convey data by modulating the electromagnetic wave used to power the sensor 100 (e.g., by modulating the current flowing through a coil of the antenna 103). The modulation in the electromagnetic wave generated by the transceiver 101 may be detected/extracted by the sensor 100. Moreover, the antenna 103 may receive data (e.g., measurement information) from the sensor 100. For example, in some non-limiting embodiments, the antenna 103 may receive data by detecting modulations in the electromagnetic wave generated by the sensor 100, e.g., by detecting modulations in the current flowing through the coil of the antenna 103. In some embodiments, the inductive element of the antenna 103 and the inductive element (e.g., inductive element 114 of FIGS. 3-8) of the sensor 100 may be in any configuration that permits adequate field strength to be achieved when the two inductive elements are brought within adequate physical proximity.

In some embodiments, the processor 105 may calculate one or more analyte concentrations based on the analyte readings received from the sensor 100. In some embodiments, the processor 105 may also generate one or more alerts and/or alarms based on the calculated analyte concentrations (e.g., if the calculated analyte concentration exceeds or falls below one or more thresholds). The calculated analyte concentrations, alerts, and/or alarms may be displayed via the user interface 107 and/or conveyed to a remote display device.

In some embodiments, the transceiver 101 may communicate (e.g., using a wireless communication standard, such as, for example, Bluetooth) with a remote device (e.g., a smartphone, personal data assistant, handheld device, or laptop computer). The remote device may receive calculated analyte concentrations, alerts, and/or alarms from the transceiver 101 and display them. Display by the remote device may be in addition to, or in the alternative to, display by the user interface 107 of the transceiver 101. For example, in some embodiments, as illustrated in FIG. 1, the transceiver 101 may include a user interface 107, but this is not required. In some alternative embodiments, the transceiver 101 may not have a user interface 107, and calculated analyte concentrations, alerts, and/or alarms may instead be displayed by a remote device.

In some non-limiting embodiments, the transceiver 101 may have some or all of the structure described in U.S. patent application Ser. No. 13/937,871, which is incorporated herein by reference in its entirety, with particular reference to FIGS. 1 and 9.

FIGS. 2-8 illustrate a non-limiting embodiment of a sensor 100 embodying aspects of the present invention that may be used in the sensor system illustrated in FIG. 1. In some embodiments, the sensor 100 may be an optical sensor. In one non-limiting embodiment, sensor 100 includes a sensor housing 102 (i.e., body, shell, or capsule). In exemplary embodiments, sensor housing 102 may be formed from a suitable, optically transmissive polymeric material, such as, for example, acrylic polymers (e.g., polymethylmethacrylate (PMMA)).

Figure 5:
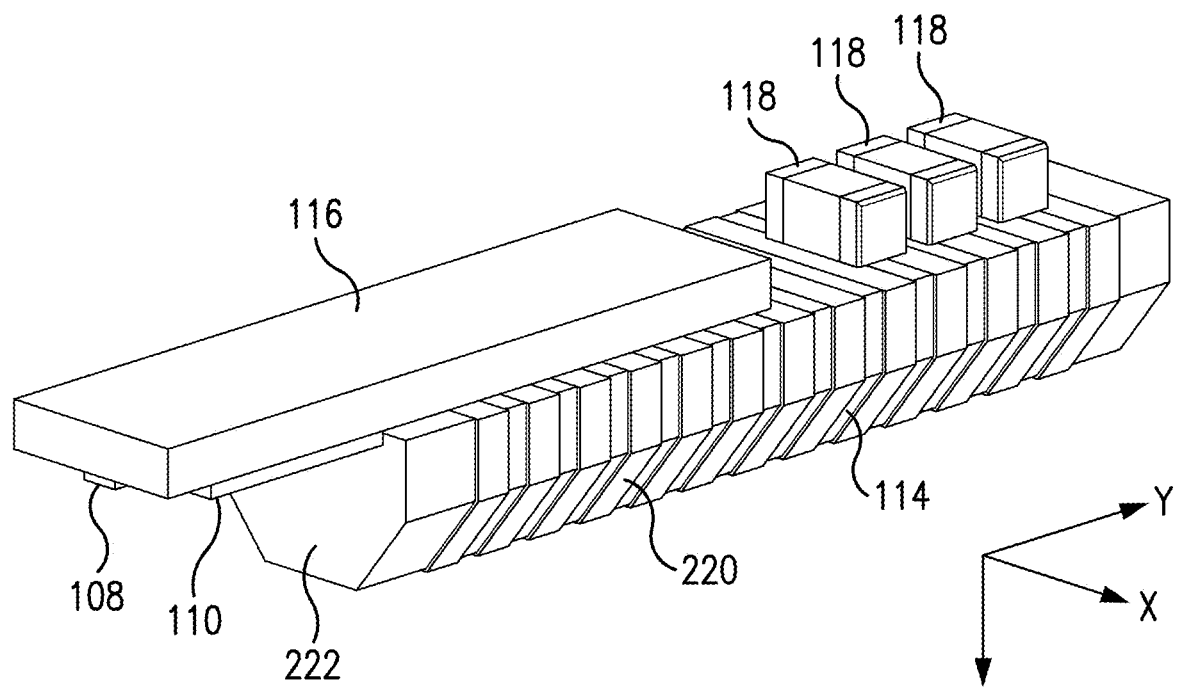
Figure 6:
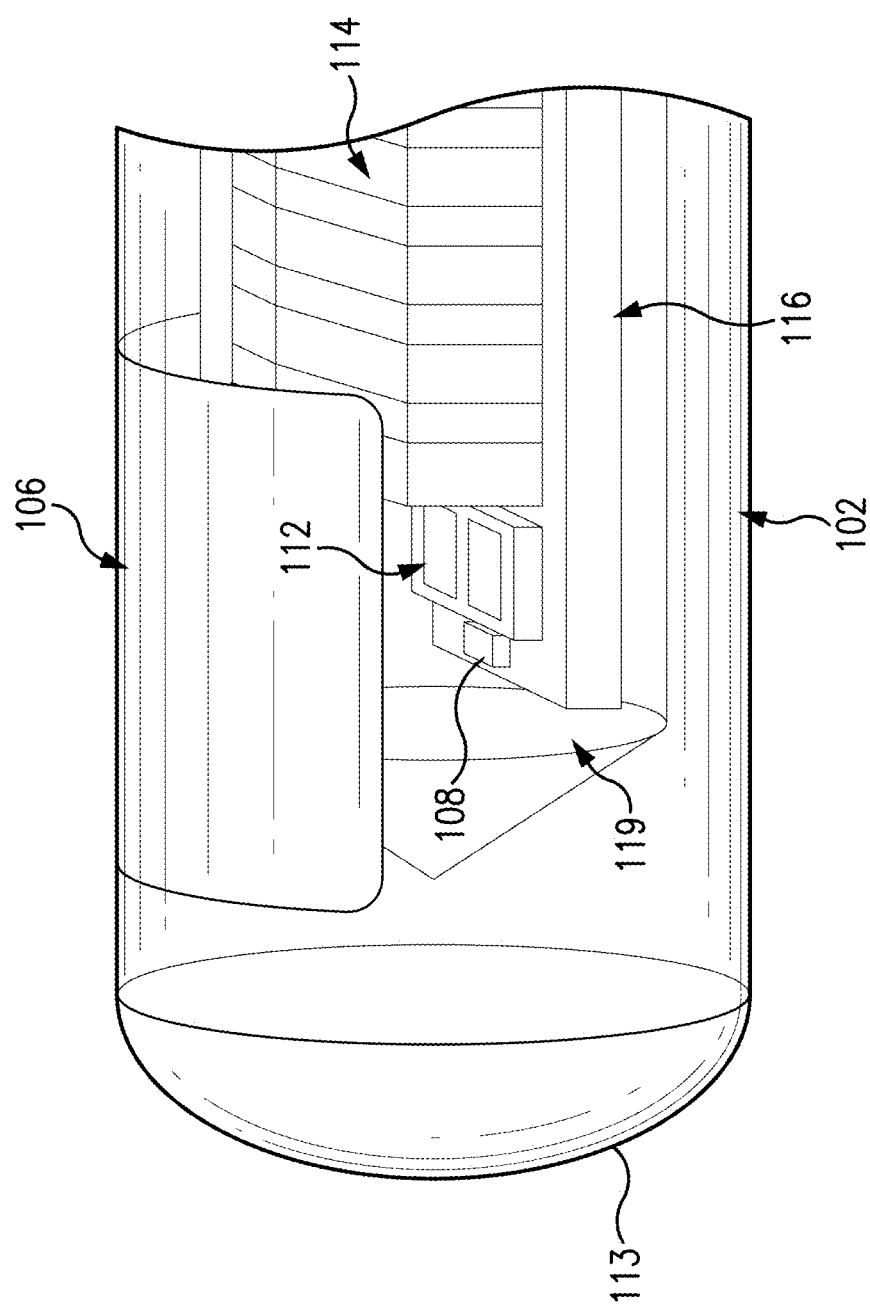
FIG. 6 illustrates a side view of a sensor embodying aspects of the present invention.
Figure 7:
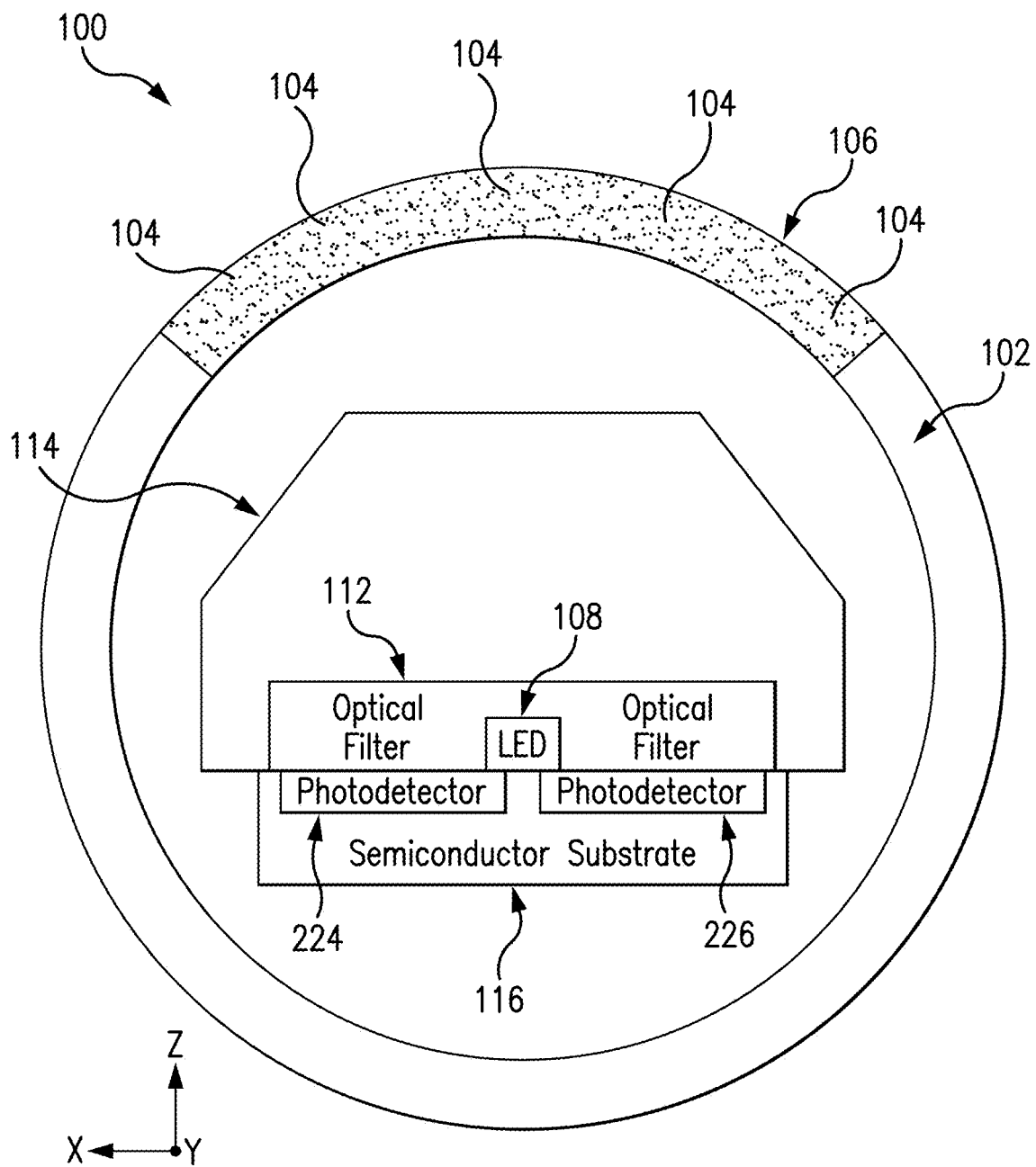
FIG. 7 illustrates a cross-sectional end view of a sensor embodying aspects of the present invention.
Figure 8:
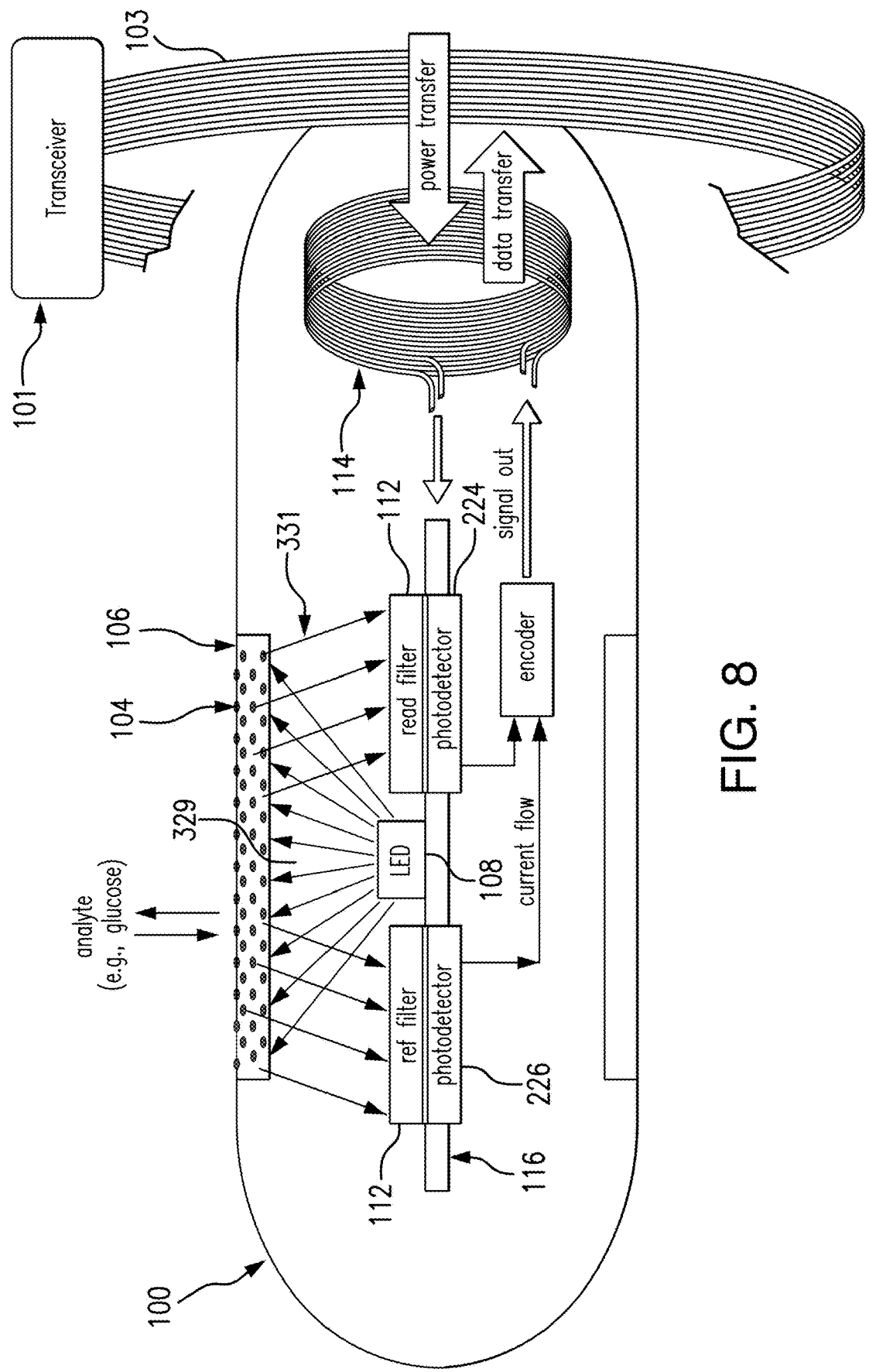
FIG. 8 illustrates a cross-sectional side view of a sensor in operation in accordance with an embodiment of the present invention.

In some embodiments, as illustrated in FIGS. 2-8, the sensor 100 may include indicator molecules 104 (see, e.g., FIGS. 7 and 8). Indicator molecules 104 may be fluorescent indicator molecules or absorption indicator molecules. In some non-limiting embodiments, the indicator molecules 104 may be as described in U.S. Pat. No. 6,344,360 or U.S. patent application Ser. No. 13/937,871, which are incorporated herein by reference in their entireties. In some non-limiting embodiments, sensor 100 may include an indicator element 106. In some non-limiting embodiments, the indicator element 106 may be a polymer graft (e.g., a matrix layer or hydrogel) coated or embedded on at least a portion of the exterior surface of the sensor housing 102, with the indicator molecules 104 distributed throughout the graft. The indicator element 106 may be embedded within the sensor housing 102 and/or cover the entire surface of sensor housing 102 or only one or more portions of the surface of housing 102. Similarly, the indicator molecules 104 may be distributed throughout the entire indicator element 106 or only throughout one or more portions of the indicator element 106.

In some embodiments, as illustrated in FIGS. 3-8, the sensor 100 may include a light source 108, which may be, for example, a light emitting diode (LED) or other light source that emits light over a range of wavelengths that interact with the indicator molecules 104.

In some embodiments, as illustrated in FIGS. 3-8, the sensor 100 may also include one or more photodetectors 110 (e.g., photodiodes, phototransistors, photoresistors, or other photosensitive elements) which, in the case of a fluorescence-based sensor, is sensitive to fluorescent light emitted by the indicator molecules 104 such that a signal is generated by the photodetector 110 in response thereto that is indicative of the level of fluorescence of the indicator molecules and, thus, the amount of analyte of interest (e.g., glucose).

In some embodiments, as illustrated in FIG. 8, the sensor 100 my include one or more optical filters 112, such as high pass or band pass filters, that may cover a photosensitive side of the one or more photodetectors 110.

In some embodiments, as shown in FIG. 8, the sensor 100 may be wholly self-contained. In other words, the sensor may be constructed in such a way that no electrical leads extend into or out of the sensor housing 102 to supply power to the sensor (e.g., for driving the light source 108) or to convey signals from the sensor 100. Instead, in some embodiments, the sensor 100 may be powered by an external power source (e.g., external transceiver 101). For example, the external power source may generate a magnetic field to induce a current in an inductive element 114 (e.g., a coil or other inductive element). Additionally, the sensor 100 may use the inductive element 114 to communicate information to an external sensor reader (e.g., transceiver 101). In some embodiments, the external power source and data reader may be the same device (e.g., transceiver 101). Although, in FIG. 8, antenna 103 of transceiver 101 is illustrated as a coil that wraps around the sensor 100, this is not required. In some alternative embodiments, the sensor may have a different configuration, such as, for example, those described in U.S. patent application Ser. No. 13/650,016, which is incorporated herein by reference in its entirety, with particular reference to FIGS. 2A-2C, or those described in U.S. patent application Ser. No. 13/937,871, which is incorporated herein by reference in its entirety.

In some embodiments, sensor 100 may include a semiconductor substrate 116 and circuitry may be fabricated in the semiconductor substrate 116. The circuitry may include analog and/or digital circuitry. In some embodiments, the circuitry may incorporate some or all of the structure described in U.S. patent application Ser. No. 13/650,016, which is incorporated herein by reference in its entirety, with particular reference to FIG. 11D. Also, although in some preferred embodiments the circuitry is fabricated in the semiconductor substrate 116, in alternative embodiments, a portion or all of the circuitry may be mounted or otherwise attached to the semiconductor substrate 116. In other words, in alternative embodiments, a portion or all of the circuitry may include discrete circuit elements, an integrated circuit (e.g., an application specific integrated circuit (ASIC)) and/or other electronic components discrete and may be secured to the semiconductor substrate 116, which may provide communication paths between the various secured components.

In some embodiments, the one or more photodetectors 110 may be mounted on the semiconductor substrate 116, but, in some preferred embodiments, the one or more photodetectors 110 may be fabricated in the semiconductor substrate 116. In some embodiments, the light source 108 may be mounted on the semiconductor substrate 116. For example, in a non-limiting embodiment, the light source 108 may be flip-chip mounted on the semiconductor substrate 116. However, in some embodiments, the light source 108 may be fabricated in the semiconductor substrate 116.

In some embodiments, the sensor 100 may include one or more capacitors 118. The one or more capacitors 118 may be, for example, one or more tuning capacitors and/or one or more regulation capacitors. Further, the one or more capacitors 118 may be in addition to one or more capacitors fabricated in the semiconductor substrate 116.

In some embodiments, the sensor 100 may include a reflector 119 (i.e., mirror). Reflector 119 may be attached to the semiconductor substrate 116 at an end thereof (see, FIG. 3). In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from reaching the axial end of the sensor 100.

According to one aspect of the invention, an application for which the sensor 100 was developed (although by no means the only application for which it is suitable) is measuring various biological analytes in the living body of an animal (including a human). For example, sensor 100 may be used to measure glucose, oxygen toxins, pharmaceuticals or other drugs, hormones, and other metabolic analytes in, for example, the human body. The specific composition of the indicator element 106 and the indicator molecules 104 therein may vary depending on the particular analyte the sensor is to be used to detect and/or where the sensor is to be used to detect the analyte (i.e., in interstitial fluid). Preferably, however, indicator element 106 should facilitate exposure of the indicator molecules to the analyte. Also, it is preferred that the optical characteristics of the indicator molecules (e.g., the level of fluorescence of fluorescent indicator molecules) be a function of the concentration of the specific analyte to which the indicator molecules are exposed.

Figure 4:
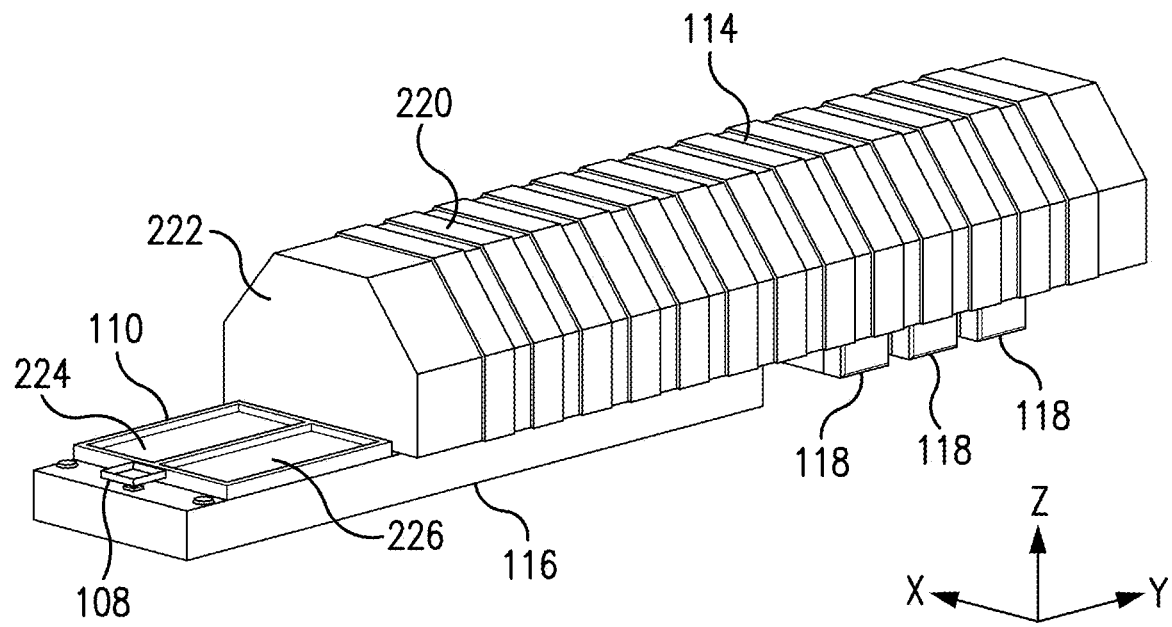
FIGS. 4 and 5 illustrate perspective views of sensor components within the sensor body/shell/capsule of a sensor embodying aspects of the present invention.

FIGS. 4 and 5 illustrate perspective views of the sensor 100. In FIGS. 4 and 5, the sensor housing 102, filters 112, and the reflector 119, which may be included in some embodiments of the sensor 100, are not illustrated. In some embodiments, as shown in FIGS. 4 and 5, the inductive element 114 may comprise a coil 220. In some embodiments, the coil 220 may be a copper coil, but, in some alternative embodiments, other conductive materials, such as, for example and without limitation, screen printed gold, may be used. In some embodiments, the coil 220 is formed around a ferrite core 222. Although core 222 is ferrite in some embodiments, in some alternative embodiments, other core materials may be used. In some embodiments, coil 220 is not formed around a core. Although coil 220 is illustrated as a cylindrical coil in FIGS. 4 and 5, in other embodiments, coil 220 may be a different type of coil, such as, for example, a flat coil.

In some embodiments, coil 220 is formed on ferrite core 222 by printing the coil 220 around the ferrite core 222 such that the major axis of the coil 220 (magnetically) is parallel to the longitudinal axis of the ferrite core 222. A non-limiting example of a coil printed on a ferrite core is described in U.S. Pat. No. 7,800,078, which is incorporated herein by reference in its entirety. In an alternative embodiment, coil 220 may be a wire-wound coil. However, embodiments in which coil 220 is a printed coil as opposed to a wire-wound coil are preferred because each wire-wound coil is slightly different in characteristics due to manufacturing tolerances, and it may be necessary to individually tune each sensor that uses a wire-wound coil to properly match the frequency of operation with the associated antenna. Printed coils, by contrast, may be manufactured using automated techniques that provide a high degree of reproducibility and homogeneity in physical characteristics, as well as reliability, which may be important for implant applications, and may increase cost-effectiveness in manufacturing.

In some embodiments, a dielectric layer may be printed on top of the coil 220. The dielectric layer may be, in a non-limiting embodiment, a glass based insulator that is screen printed and fired onto the coil 220. In an exemplary embodiment, the one or more capacitors 118 and the semiconductor substrate 116 may be mounted on vias through the dielectric.

In the illustrated embodiment, the one or more photodetectors 110 include a first photodetector 224 and a second photodetector 226. First and second photodetectors 224 and 226 may be mounted on or fabricated in the semiconductor substrate 116.

FIGS. 6 and 7 illustrate side and cross-sectional views, respectively, of the sensor 100 according to one embodiment. As illustrated in FIGS. 6 and 7, the light source 108 may be positioned to emit light that travels within the sensor housing 102 and reaches the indicator molecules 104 of the indicator element 106, and the photodetectors 110, which may be located beneath filters 112, may be positioned to receive light from the indicator molecules 104 of the indicator element 106.

In operation, as shown in FIG. 8, the light source 108 (e.g., an LED) may emit excitation light 329 that travels within the sensor housing 102 and reaches the indicator molecules 104 of the indicator element 106. In a non-limiting embodiment, the excitation light 329 may cause the indicator molecules 104 distributed in indicator element 106 to fluoresce. As the indicator element 106 may be permeable to the analyte (e.g., glucose) in the medium (e.g., blood or interstitial fluid) into which the sensor 100 is implanted, the indicator molecules 104 in the indicator element 106 may interact with the analyte in the medium and, when irradiated by the excitation light 329, may emit indicator fluorescent light 331 indicative of the presence and/or concentration of the analyte in the medium.

Figure 3:
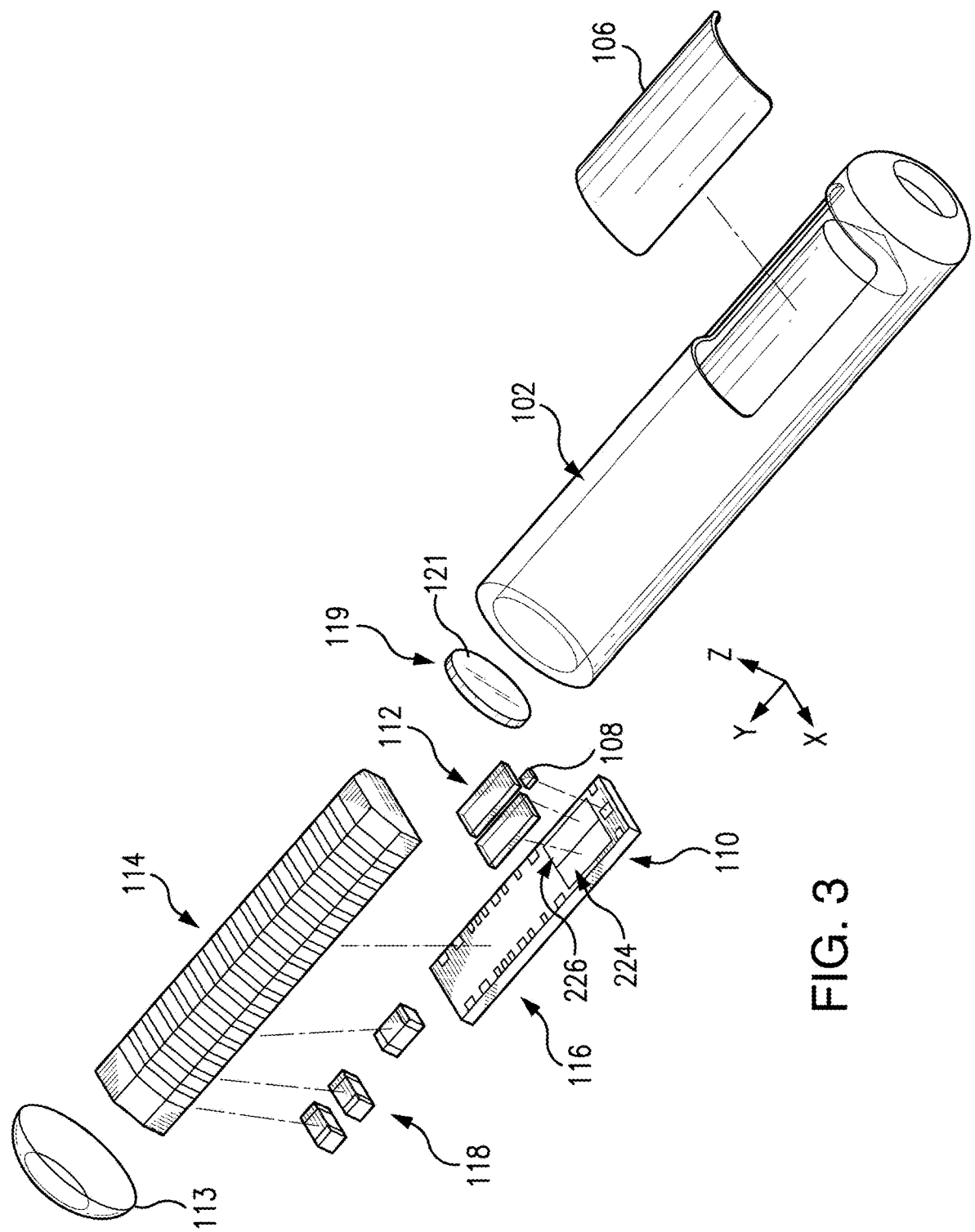
FIG. 3 illustrates an exploded view of a sensor embodying aspects of the present invention.

The photodetectors 224 and 226 are used to receive light (see FIG. 3). Each photodetector 224 and 226 may be covered by a filter 112 that allows only a certain subset of wavelengths of light to pass through (see FIG. 3). The filters 112 may be thin film (e.g., dichroic) filters deposited on glass, and the filters 112 may pass only a narrow band of wavelengths and otherwise reflect the received light. The filters 112 may be identical (e.g., both filters 112 may allow signal light to pass) or different (e.g., one filter 112 may allow signal light to pass, and the other filter 112 may allow reference light to pass).

Photodetector 226 may be a reference photodetector, and the filter 112 may pass light at the same wavelength as the wavelength of the excitation light 329 emitted from the light source 108 (e.g., 378 nm). Photodetector 224 may be a signal photodetector that detects the amount of fluoresced light 331 that is emitted from the indicator molecules 104 in the indicator element 106. In some non-limiting embodiments, the signal filter 112 (i.e., the filter 112 covering photodetector 224) may pass light in the range of about 400 nm to 500 nm. Higher analyte levels may correspond to a greater amount of fluorescence of the molecules 104 in the indicator element 106, and therefore, a greater amount of photons striking the signal photodetector 224.

Embodiments of the present invention may include one or more of several possible solutions to the light-blocking and/or indicator element deterioration problems described above.

Figure 9:
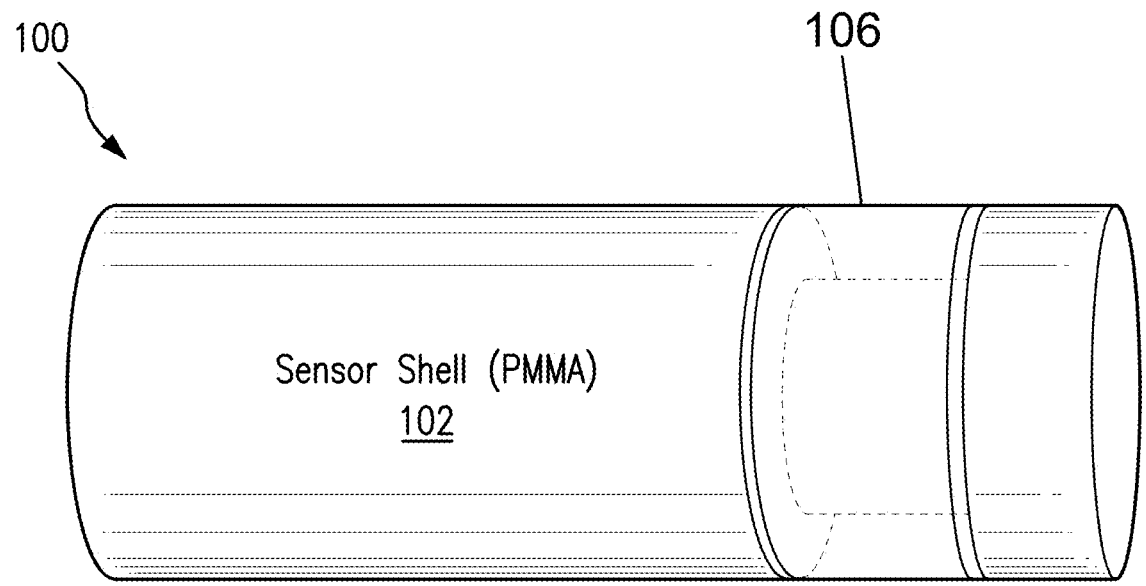
FIGS. 9 and 10 illustrate a side view of a sensor, without and with a membrane over the indicator element, respectively, in accordance with an embodiment of the present invention.
Figure 10:
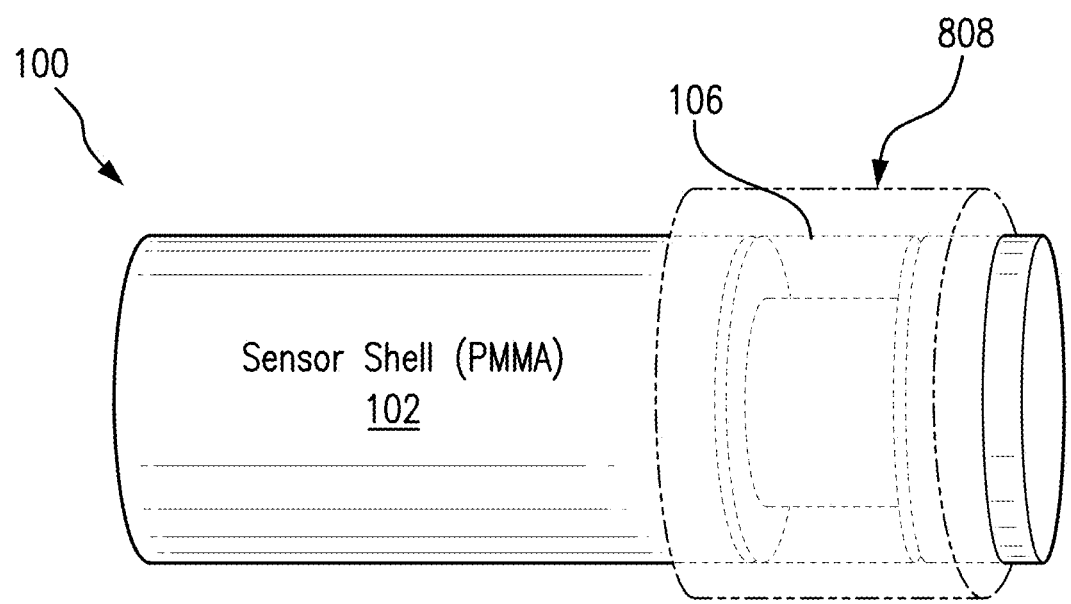

FIGS. 9 and 10 illustrate a sensor 100 in accordance with an embodiment of the present invention. In some non-limiting embodiments, the sensor 100 may have a sensor housing/shell 102 and an indicator element 106 embedded within and/or covering at least a portion of the housing 102. The indicator element 106 may include indicator molecules 104 (see, e.g., FIGS. 7 and 8).

In regard to indicator element deterioration, as explained above, white blood cells, including neutrophils, may attack an implanted sensor 100. The neutrophils release, inter alia, hydrogen peroxide, which may degrade indicator molecules (e.g., by oxidizing a boronate group of an indicator molecule and disabling the ability of the indicator molecule to bind glucose).

In some non-limiting embodiments, the indicator element 106 may a have layer (e.g., a thin layer such as, for example and without limitation, a 10 nm thick layer) on the outside of the indicator element 106. In some embodiments, the layer may protect against indicator molecule degradation. In some embodiments, the layer may comprise platinum, and the platinum may be sputtered onto the outside surface of the indicator element 106, which includes the indicator molecules 104 (see, e.g., FIGS. 7 and 8). Platinum rapidly catalyzes the conversion of hydrogen peroxide into water and oxygen, which are harmless to the sensor. The rate of this reaction is much faster than the boronate oxidation; thus, the platinum provides some protection against oxidation by reactive oxygen species. Although platinum is the catalyst of the conversion of hydrogen peroxide into water and oxygen in some embodiments, in some alternative embodiments, other catalysts of this reaction, such as, for example, palladium or catalase, may be used for the thin layer instead of or in addition to platinum.

Figure 11:
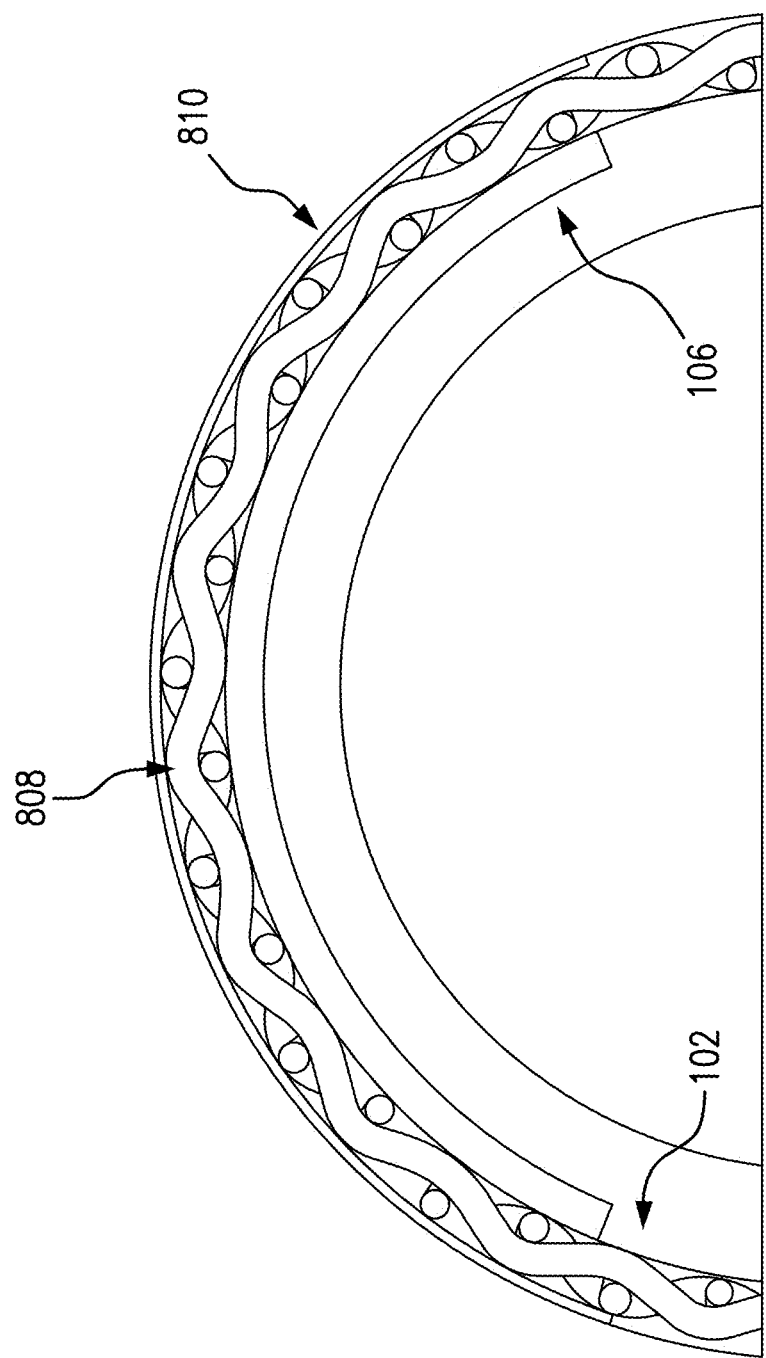
FIGS. 11 and 12 illustrate a cross-sectional view of a sensor embodying aspects of the present invention.

In some embodiments, as illustrated in FIG. 10, the sensor 100 may have a membrane 808 over the indicator element 106 (and over any layer/film on the outside of the indicator element 106). The membrane 808 may be opaque and, therefore, perform a light-blocking function. In other words, the opaque nature of the membrane may serve the function of effectively blocking extraneous light. In some non-limiting embodiments, the sensor 100 may include both a membrane 808 that is opaque and an additional layer, such as a layer 810 as illustrated in FIG. 11, over the membrane 808. However, in other embodiments, only the opaque membrane 808 is used to block light, and, in these embodiments, the sensor 100 does not include an additional layer, such as the layer 810 illustrated in FIG. 11, over the membrane 808.

In some non-limiting embodiments, the opaque membrane 808 may be physically attached over the indicator element 106 after boring an additional, smaller well into the capsule/housing 102. In some non-limiting embodiments, the membrane 808 may be made of a mesh material, such as, for example, as a woven, non-woven, sintered, precipitated, or electrospun nylon. However, this is not required, and, in some alternative embodiments, the membrane 808 may be made of another material, such as, for example, cellulose acetate, polytetrafluoroethylene, polyethylene teraphthlate, polypropylene, polyvinyl alcohol, polybutylene terephthalate, polyether ether ketone, polyanhydride, polyamide, polyvinylchloride, polyethersulfone, polyvinylidene difluoride, polycarbonate, or derivatives thereof.

In some embodiments, the membrane 808 may be porous. In other words, the membrane 808 may be structured so that it channels one or more analytes (e.g., glucose) to the indicator element 106. For example, in one non-limiting embodiment, the membrane 808 has small pores (e.g., pores having a pore size of microns or less) that block the passage of white blood cells (e.g., neutrophils), which are typically between 6 and 12 microns in diameter, from reaching the underlying indicator element 106 to attack it. The small pores, however, would at the same time be large enough to allow the analyte to reach the indicator element 106. In this way, a porous membrane 808 having small pores would increase sensor longevity while not affecting the ability of the sensor 100 to measure the concentration of an analyte. In some embodiments, polymers that control or reduce the body's response to an implant (i.e., the foreign body response) such as polyethylene oxides (PEO), hydroxy acrylates (HEMA), or fluoropolymers could be coated onto any of the membranes 808 (e.g., polytetrafluoroethylene (PTFE) coated onto polyethylene teraphthlate (PET) or PEO coated onto nylon).

In some embodiments, the membrane 808 may be made from a material that does not react adversely to the body's defenses. In non-limiting embodiments, the material from which the membrane 808 is made may be porous (e.g., to allow and analyte, such as glucose, to flow through it) and/or opaque (e.g., to prevent light from traveling through it). For example, in some embodiments, the membrane material may be a hydrophilic material, such as, for example, nylon or cellulose acetate. In other embodiments, the membrane material may be a hydrophobic material, such as, for example, polyethylene terephthalate or polytetrafluoroethylene.

Figure 12:
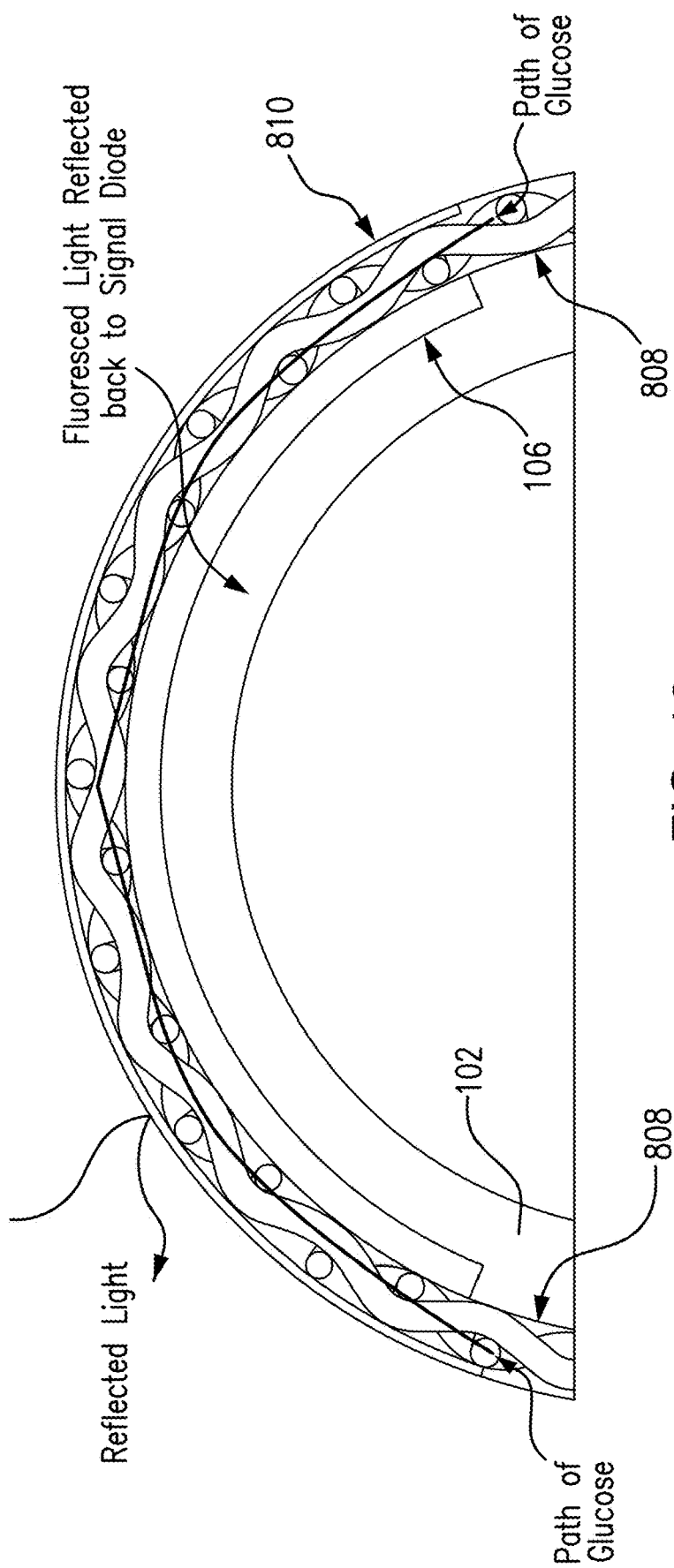

FIGS. 11 and 12 illustrate a cross-sectional view of a sensor 100 having a membrane 808 in accordance with another embodiment of the present invention. As illustrated in FIGS. 11 and 12, the indicator element 106 of sensor 100 may be covered by a membrane 808, and the sensor 100 may additionally include a thin layer 810, which may also block light. For example, in some embodiments, the layer 810 may prevent excitation light 329 from the light source 108 (see FIG. 8) from escaping the sensor housing/capsule 102 and prevent undesirable light entering the sensor housing/capsule 102. This undesirable light may be from outside the body and/or may be reflected or fluoresced excitation light being returned from body tissue. Reduction of each type of undesirable light would improve sensor accuracy. In one non-limiting embodiment, the layer 810 may be a mirror. In one non-limiting embodiment, an additional smaller well may be bored into the capsule/housing 102, a membrane 108 may be physically attached over the indicator element 106, and an additional blocking layer 810 may then be attached.

In some embodiments, the membrane 808 may channel an analyte to the indicator element 106, while the layer 810 and/or membrane 808 simultaneously block any errant light.

The membrane 808 may be porous such that it does not physically block the analyte (e.g., glucose) from reaching the indicator element 106. Furthermore, the membrane 808 may have channels small enough to block white blood cells from reaching the indicator element 106, but large enough to allow for the passage of red blood cells and glucose molecules.

In some non-limiting embodiments, the layer 810 may be a material that does not adversely react to the body's defenses. In one non-limiting embodiment, platinum may serve as both the material for the membrane 808 and as the material for the layer 810 because platinum catalyzes hydrogen peroxide species and reduces the deterioration of the indicator element 106 that would otherwise occur, while also blocking extraneous light from over stimulating the indicator element 106. With a platinum membrane 808 in place, hydrogen peroxide, which is produced by a patient's white blood cells through the disproportionation of superoxide ($O_2^-$), would quickly be catalyzed to water and oxygen, which are harmless to the sensor 100. Thus, a platinum membrane 808 may increase the lifetime of the sensor 100 in the body.

In some alternative embodiments, polymers, such as, for example, nylon, cellulose acetate, polytetrafluoroethylene (PTFE), polyethylene teraphthlate (PET), polypropylene (PP), polyvinyl alcohol (PVA), polybutylene terephthalate (PBT), polyether ether ketone (PEEK), polyanhydride, polyamide, polyvinylchloride (PVC), polyethersulfone (PES), polyvinylidene difluoride (PVDF), or polycarbonate may additionally or alternatively be used as the membrane material.

Figure 13:
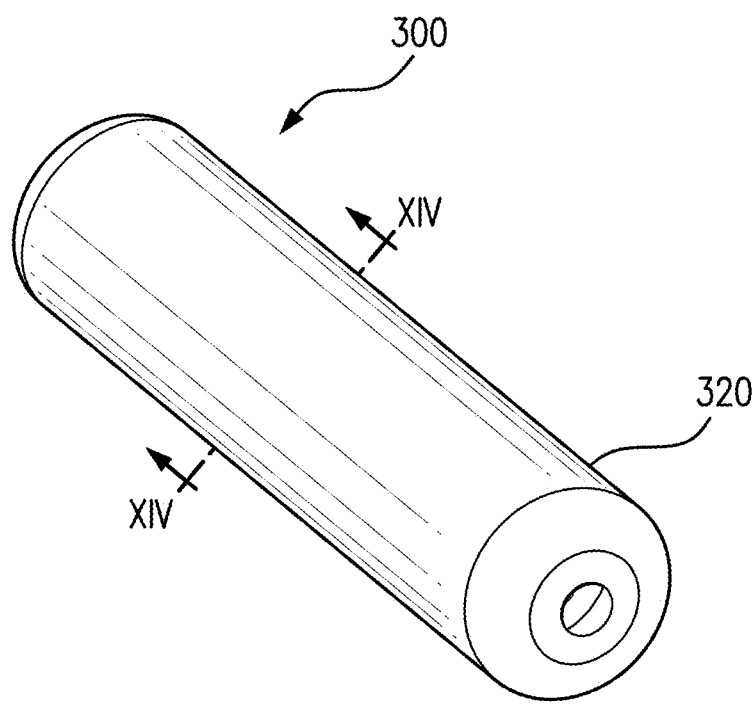
FIG. 13 is a perspective view of an alternate embodiment of a sensor embodying aspects of the present invention and comprising an opaque diffusion membrane substantially, or totally, covering the housing of a sensor.

An alternative solution to the light blocking and immune response issues is an opaque diffusion membrane that is configured to both block light from entering or exiting the sensor housing and prevent reactive oxygen species-generating cells from direct tissue contact with the indicator element. A sensor assembly embodying aspects of the invention of this alternative solution is represented by reference number 300 in FIG. 13, which is a perspective view of the sensor assembly. Sensor assembly 300 comprises an implantable sensor, such as sensor 100 described above, covered or substantially covered by an opaque diffusion membrane 320.

Figure 14:
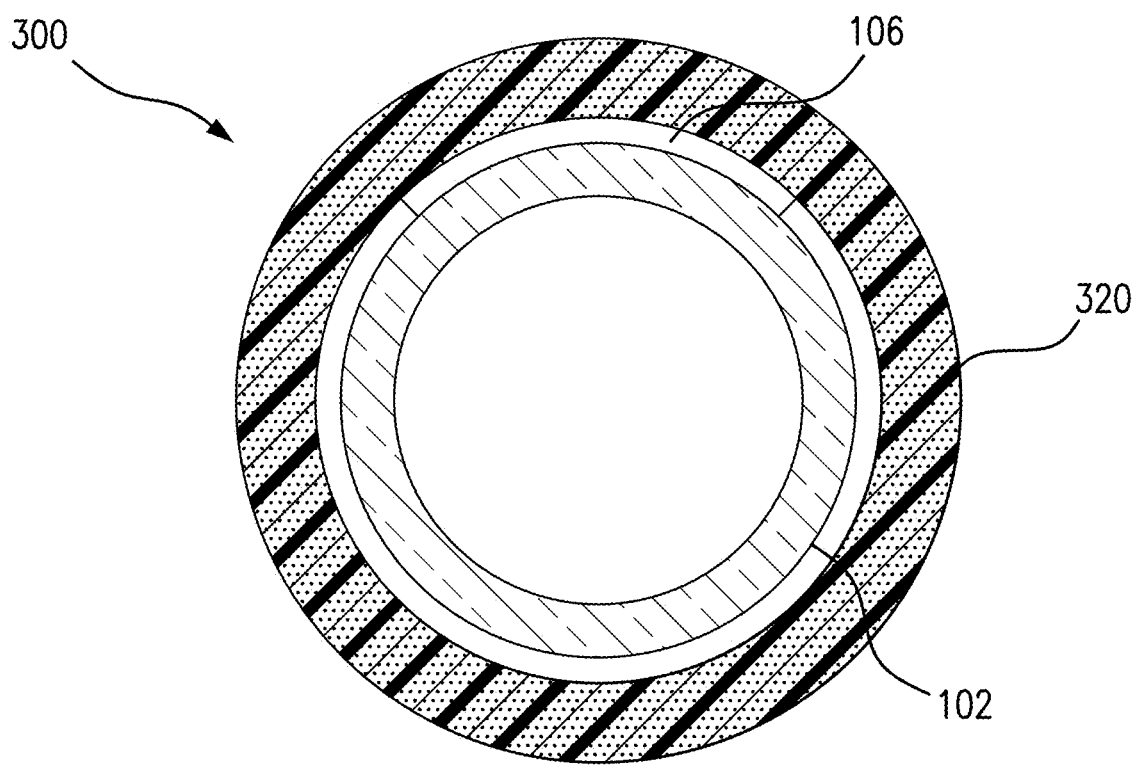
FIG. 14 is a transverse cross-section of the sensor and opaque diffusion membrane along the line XIV-XIV in FIG. 13.

FIG. 14 is a transverse cross-section of the sensor assembly 300. For simplicity of the figure, the internal components of the sensor, such as the light source, filters, antennae, etc., are not shown in FIG. 14. The sensor assembly 300 may comprise a sensor housing 102 which, as described above, may comprise a suitable, optically transmissive polymer material, such as PMMA. Further, as described above, the sensor may include an indicator element 106 coated on or embedded in at least a portion of the exterior surface of the housing 102. The diffusion membrane 320 is disposed over the sensor housing 102 and indicator element 106. It should be noted that the relative thicknesses of the various layers of the sensor assembly 300 shown in FIG. 14 are for clarity of illustration and should not be viewed as limiting.

Preferably, the diffusion membrane 320 is made of a material that does not react adversely to the body's defenses but can also be effectively manipulated to be both porous to allow an analyte (e.g., glucose) to flow through the membrane and opaque to substantially prevent light transmission through the membrane. Suitable materials include, for example, nylon or cellulose acetate because such materials are hydrophilic and can therefore be expected to allow an analyte solution (e.g., a glucose solution) to pass through pores formed in the material. Ready passage of the analyte solution through the membrane pores will facilitate analyte readings with less of a time lag. In addition, porous membranes formed from hydrophobic materials, such as polypropylene, polyethylene terephthalate ("PET"), and polytetrafluoroethylene ("PTFE"), can be made hydrophilic by known surface treatments methods, such as oxygen plasma treatment or chemical treatments to generate hydrophilic surface moieties or by grafting of hydrophilic polymers onto the surface of hydrophobic materials, and thus allow facile diffusion of analyte solutions.

One example of an opaque diffusion membrane embodying aspects of the invention may comprise a porous PET tube loaded with an opaque colorant (e.g., TiO2, carbon black). The total amount of colorant added to the PET may be altered such that no measurable light transmission through the diffusion membrane can be detected at the wavelengths of interest. For example, the amount of colorant added to the diffusion membrane material may be increased to a point at which no measurable light is transmitted through the PET (or other membrane material) layer.

Preferably, in one embodiment, the opaque diffusion membrane 320 extends over the entire sensor housing 102 covering substantially any and all light paths into or out of the sensor housing. Preferably, the membrane would include end covers with or without wrapped ends.

A goal is to match light-blocking ability of the membrane 320 with the porosity of the membrane material. Accordingly, the percent open area of the membrane material is preferably sufficiently small (e.g., 6-25%) to block light, but still has sufficient porosity to allow diffusion. In one exemplary embodiment, PET membrane material could be tracked, etched, or laser drilled to add pores. In some non-limiting embodiments, the pores added to the PET membrane material may have a size at the exit that prevents leukocytes (white blood cells), which have a size of approximately 7-80 microns, from passing through the pores. For example, in one non-limiting embodiment, the pores may have a size of approximately 5-7 microns at the exit.

In some non-limiting embodiments, a characteristic of the diffusion membrane 320 may be to provide maximum distance between the white blood cells and the indicator element 106. Thus, in one embodiment of a diffusion membrane 320 embodying aspects of the invention, the membrane 320 comprises a PET layer having a thickness of approximately 25 to 50 microns to keep immune cells (e.g., white blood cells) at a sufficient distance away from the indicator element 106.

Figure 15:
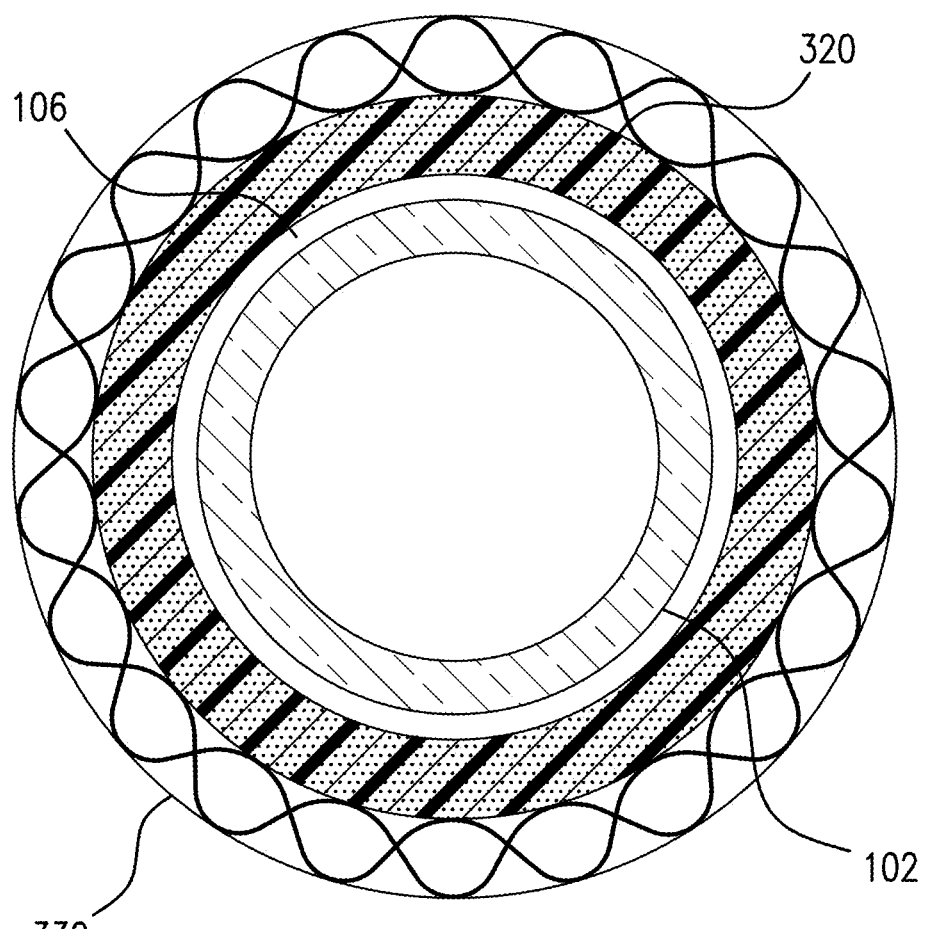
FIG. 15 is an alternate embodiment of a sensor covered with an opaque diffusion membrane.

As shown in FIG. 15, another embodiment of a diffusion membrane embodying aspects of the invention is configured to maintain a sufficient distance between white blood cells and the indicator element 106 and employs a combination of materials comprising a relatively thick (e.g., 50-200 micron) porous, torturous path material 330 disposed either beneath or on top of the porous PET (or other material) layer 320 to provide an additional optically isolating layer and to further increase the distance between the immune cell (e.g., white blood cells) and the indicator element 106. A suitable material for the torturous path layer includes nylon. The torturous path material 330 provides a longer path through which ROS produced by the white blood cells would need to travel before reaching analyte-sensing indicator element 106 and thereby increases the degree to which the ROS are diluted and/or degraded. Accordingly, the tortuous path material 330 enhances the white blood cell-blocking capability of such a multi-layer diffusion membrane comprising layers 320 and 330.

In some embodiments, the sensor 100 may include a plurality of membranes. For example, in some non-limiting embodiments, the sensor 100 may include one or more catalytic membranes, one or more porous immune response blocking membranes, and/or one or more light blocking membranes. In one non-limiting embodiment, the sensor 100 may include a catalytic membrane on top of the indicator element 106, a porous immune response blocking membrane on top of the catalytic membrane, and a light blocking membrane on top of the porous immune response blocking membrane. In another non-limiting embodiment, the membranes may be arranged over the indicator element 106 in a different order. In yet another non-limiting embodiment, one or more of the plurality of membranes may have one or more functions (e.g., a sensor 100 may include membrane having catalytic membrane and a membrane that blocks both light and immune response).

Figure 16A:
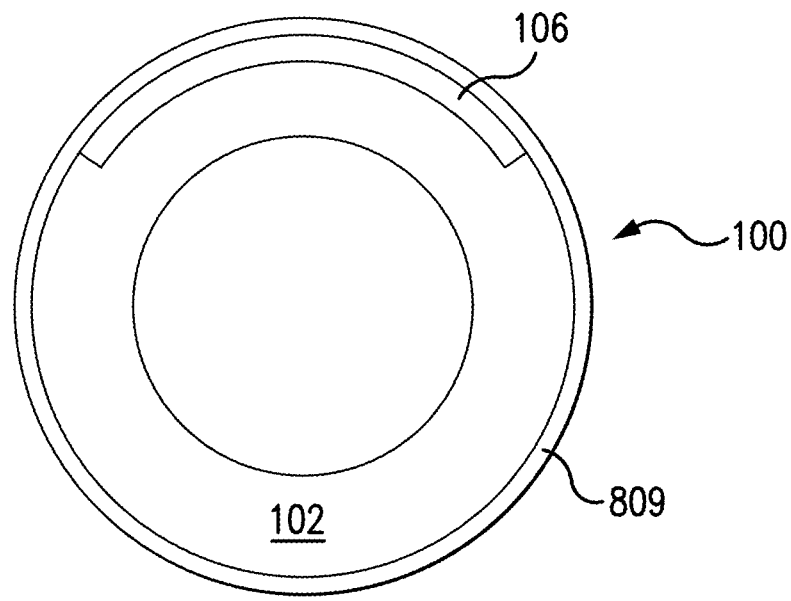
FIGS. 16A-16C illustrate a cross-sectional views of a sensor, membrane, and sensor with membrane, respectively, embodying aspects of the present invention.

FIG. 16A is a cross-sectional view of a sensor 100 embodying aspects of the present invention. In some embodiments, as shown in FIG. 16A, the sensor 100 may include a sensor housing 102 and an indicator element 106. In some embodiments, the indicator element 106 may be embedded within and/or covering at least a portion of the sensor housing 102. In some non-limiting embodiments, the sensor 100 may include a layer 809 on the outside of the indicator element 106. In some non-limiting embodiments, the layer 809 may be on all or a portion of the outside of the indicator element 106. In some non-limiting embodiments where a portion of the sensor housing 102 is not covered by the indicator element 106, the layer 809 may additionally be on all or a portion of the portion of the sensor housing 102 not covered by the indicator element 106.

Figure 16B:
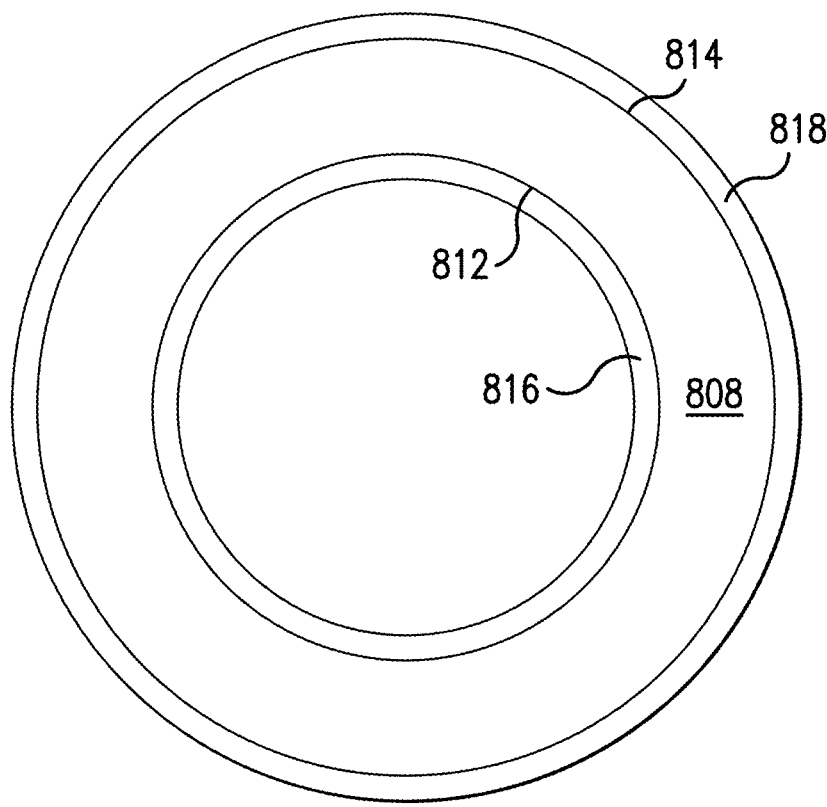

FIG. 16B is a cross-sectional view of a membrane 808 embodying aspects of the present invention. The membrane 808 may comprise an inner surface 812 and an outer surface 814. In some embodiments, the membrane 808 may include one or more of (i) a first coating 816 on the inner surface 812 and (ii) a second coating 818 on the outer surface 814.

Figure 16C:
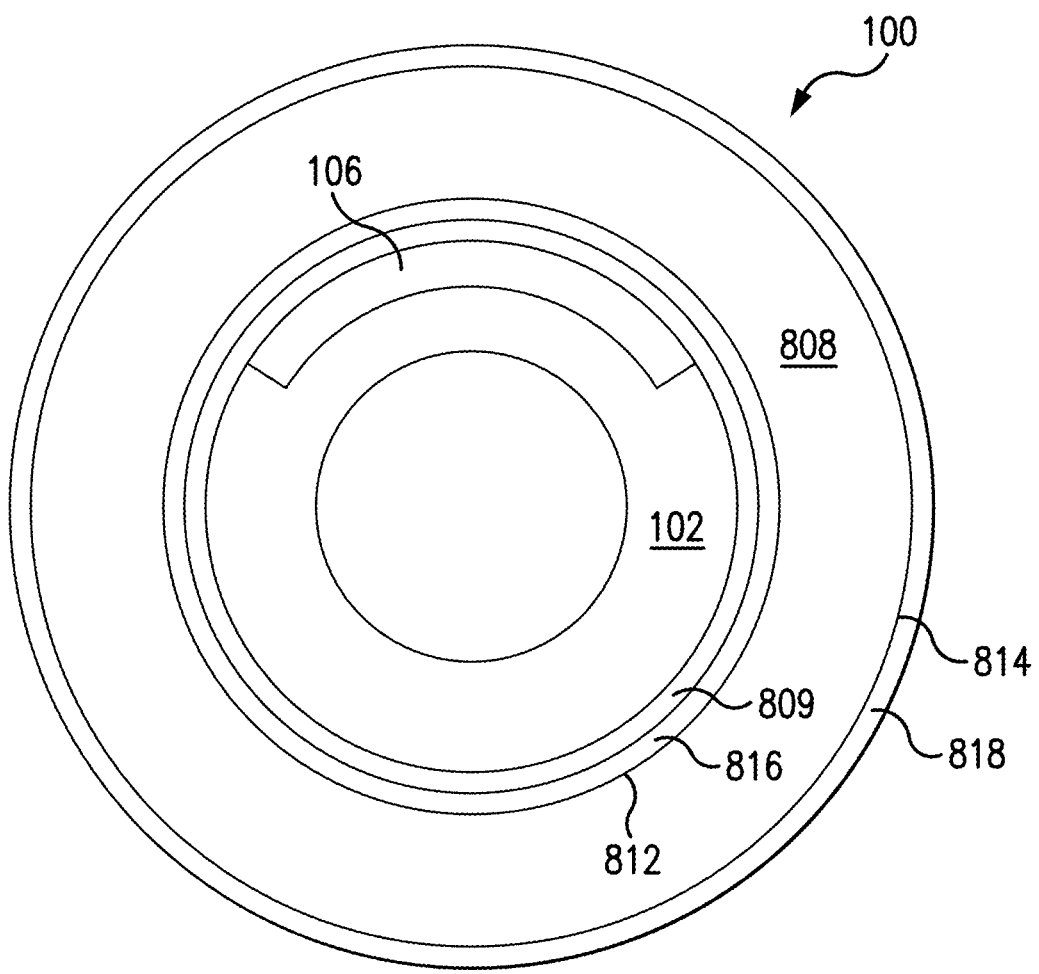

FIG. 16C is a cross-sectional view of a sensor 100 including a membrane 808 embodying aspects of the present invention. In some embodiments, the membrane 808 may be over at least a portion of the indicator element 106. In some embodiments, the membrane 808 by itself may provide some measure of in vivo oxidation protection (e.g., by virtue of it being a barrier between the ROS species and the indicator element 106. In some embodiments, the sensor 100 may include one or more of (i) the first coating 816 on the inner surface 812 of the membrane 808, (ii) the second coating 818 on the outer surface 814 of the membrane 808, and (iii) the layer 809 on the outside of the indicator element 106, which may be between the first coating 816 on the inner surface 812 of the membrane 808 and the indicator element 106.

In some embodiments, one or more of the first coating 816, the second coating 818, and the layer 809 on the outside of the indicator element 106 may reduce deterioration of the indicator element 106 by catalyzing degradation of reactive oxygen species (ROS). In some non-limiting embodiments, one or more of the first coating 816, the second coating 818, and the layer 809 on the outside of the indicator element 106 may comprise a one or more catalysts of the conversion of hydrogen peroxide into water and oxygen, such as, for example and without limitation, platinum, palladium, and catalase. In some non-limiting embodiments, the one or more catalysts of the conversion of hydrogen peroxide into water and oxygen may be sputtered on one or more of (i) the inner surface 812 of the membrane 808 (e.g., to form the first coating 816), (ii) the outer surface 814 of the membrane 808 (e.g., to form the second coating 818), and (iii) the outside of the indicator element 106 (e.g., to form the layer 809 on the outside of the indicator element 106). In some non-limiting embodiments, one or more of the first coating 816, the second coating 818, and the layer 806 may each have a thickness of, for example and without limitation, 10 nm.

In some embodiments, the membrane 808 having one or more of the first and second coatings 816 and 818 may be attached to sensor housing 102. In some embodiments, the catalyst layer 809 may be on the indicator element 106 when the membrane 808 is attached to the sensor housing 102. In some non-limiting embodiments, the membrane 808 having one or more of the first and second coatings 816 and 818 may be attached to sensor housing 102 using one or more techniques, such as, for example and without limitation, laser bonding (e.g., laser welding), biocompatible adhesive, or heat bonding.

In some embodiments, the laser bonding may use laser light in a wavelength range that is (i) not absorbed by the sensor housing 102, (ii) not absorbed by the material (e.g., nylon) of the membrane 808, and (iii) absorbed by at least the first coating 816 on the inner surface 812 of the membrane 808. In some embodiments, the laser light may also be absorbed by the second coating 818 on the outer surface 814 of the membrane 808. In some embodiments, the first coating 816 may absorb sufficient energy to create a bond between the first coating 816 of the membrane 808 and the sensor housing 102. In some non-limiting embodiments, the wavelength range may be infrared wavelengths. In some non-limiting embodiments, the laser bonding light may be centered at a wavelength falling anywhere in the range of 800-2200 nm. However, a particular wavelength of wavelength range is not required, and, in some alternative embodiments, the laser bonding may use laser light in any wavelength range that is absorbed by one or more of the sensor housing 102 and the material of the membrane 808. In some non-limiting alternative embodiments, the wavelength range may be in a range of 2 micrometers or greater. In some embodiments, the profile of the weld spot formed by laser welding may be smooth. In some embodiments, the smoothness of the weld spot may reduce irritation to the tissue in which the sensor 100 is implanted.

Figure 19:
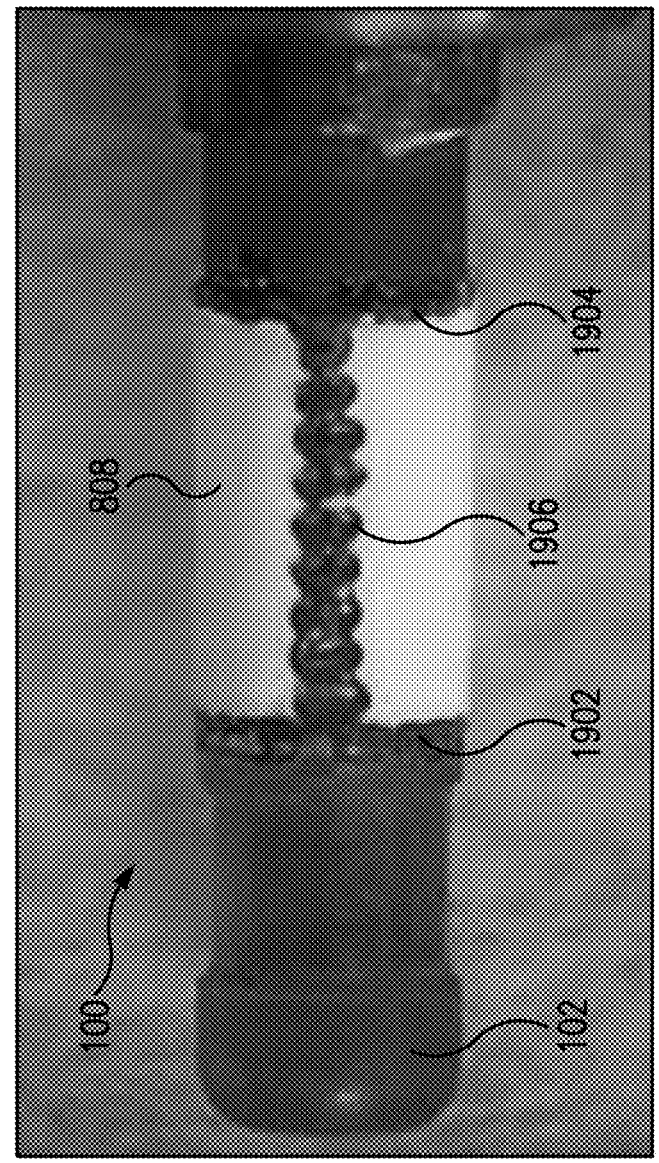
FIG. 19 illustrates a side view of a sensor having a membrane laser bonded to a sensor housing in accordance with an embodiment of the present invention.

FIG. 19 illustrates a side view of a sensor 100 having a membrane 808 laser bonded to a sensor housing 102 in accordance with an embodiment of the present invention. In some embodiments, as shown in FIG. 19, the membrane 808 may be attached to the sensor housing 102 by one or more laser welds. In some non-limiting embodiments, the one or more laser welds may include one or more of a circumferential laser weld 1902, a circumferential laser weld 1904, and a lap joint laser weld 1906. In some embodiments, each of one or more of the laser welds 1902, 1904, and 1906 may include one or more weld spots.

However, weld spots are not required, and, in some alternative embodiments, one or more of the laser welds 1902, 1904, and 1906 may not include weld spots. For example, in some alternative embodiments, each of one or more of the laser welds 1902, 1904, and 1906 may be formed by a continuous weld. In some other alternative embodiments, each of the one or more of the laser welds 1902, 1904, and 1906 may be formed by one or more weld lines (e.g., a zigzag weld line or a plurality of weld lines). In some embodiments, the one or more weld lines may be formed using a lower laser beam intensity than the laser beam used to form the laser spots.

Figure 21:
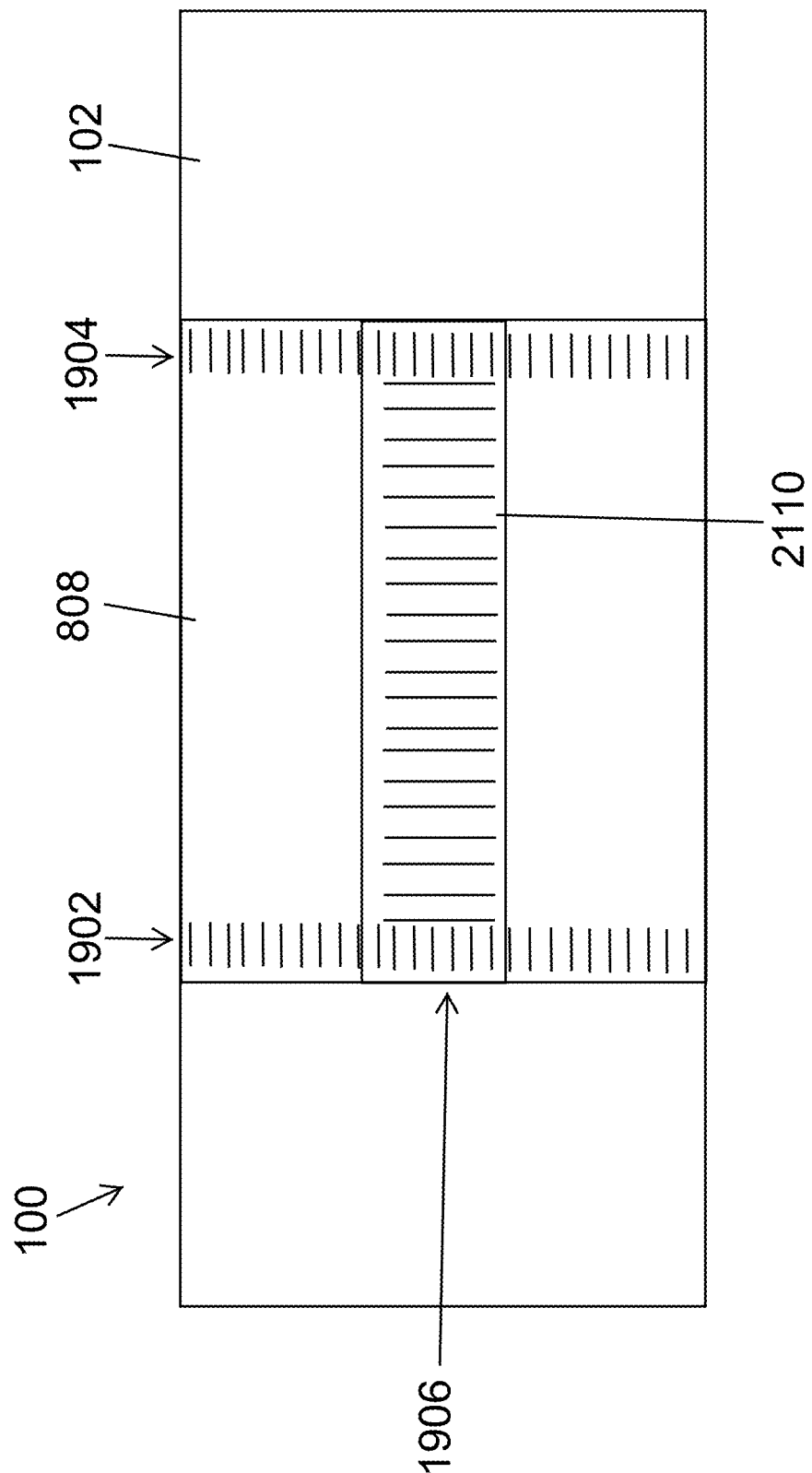
FIG. 21 illustrates a side view of a sensor having a membrane laser bonded to a sensor housing in accordance with an embodiment of the present invention.

FIG. 21 illustrates a side view of a sensor 100 having a membrane 808 laser bonded to a sensor housing 102 in accordance with a non-limiting alternative embodiment of the present invention in which the laser welds 1902, 1904, and 1906 are formed by weld lines. In some non-limiting embodiments, as shown in FIG. 21, one or more of the weld lines in the circumferential laser welds 1902 and 1904 may be perpendicular to the edge of the membrane 808. In some non-limiting embodiments, as shown in FIG. 21, one or more of the weld lines in the lap joint 1906 may be perpendicular to a longitudinal direction of a lap joint 2110 formed by the overlap of two ends of the membrane 808. In some embodiments, one or more of the weld lines may extend out of the lap joint 2110.

In some non-limiting embodiments, a transparent material fixture (e.g., a glass or quartz plate) may be used to hold the membrane 808 in place during laser bonding, and the laser light may pass through the transparent material fixture before reaching the membrane 808 and one or more of the first and second coatings 816 and 818. In some non-limiting embodiments, the use of the transparent material fixture may increase the smoothness of the weld (e.g., the weld spot, continuous weld, or weld lines). However, use of a transparent material fixture is not required, and some alternative embodiments may hold the membrane 808 in place during laser bonding in a different manner. For example and without limitation, in some alternative embodiments, string may be used to hold the membrane 808 in place during laser bonding and removed after the laser bonding is completed (or as the laser bonding is performed).

Figure 20:
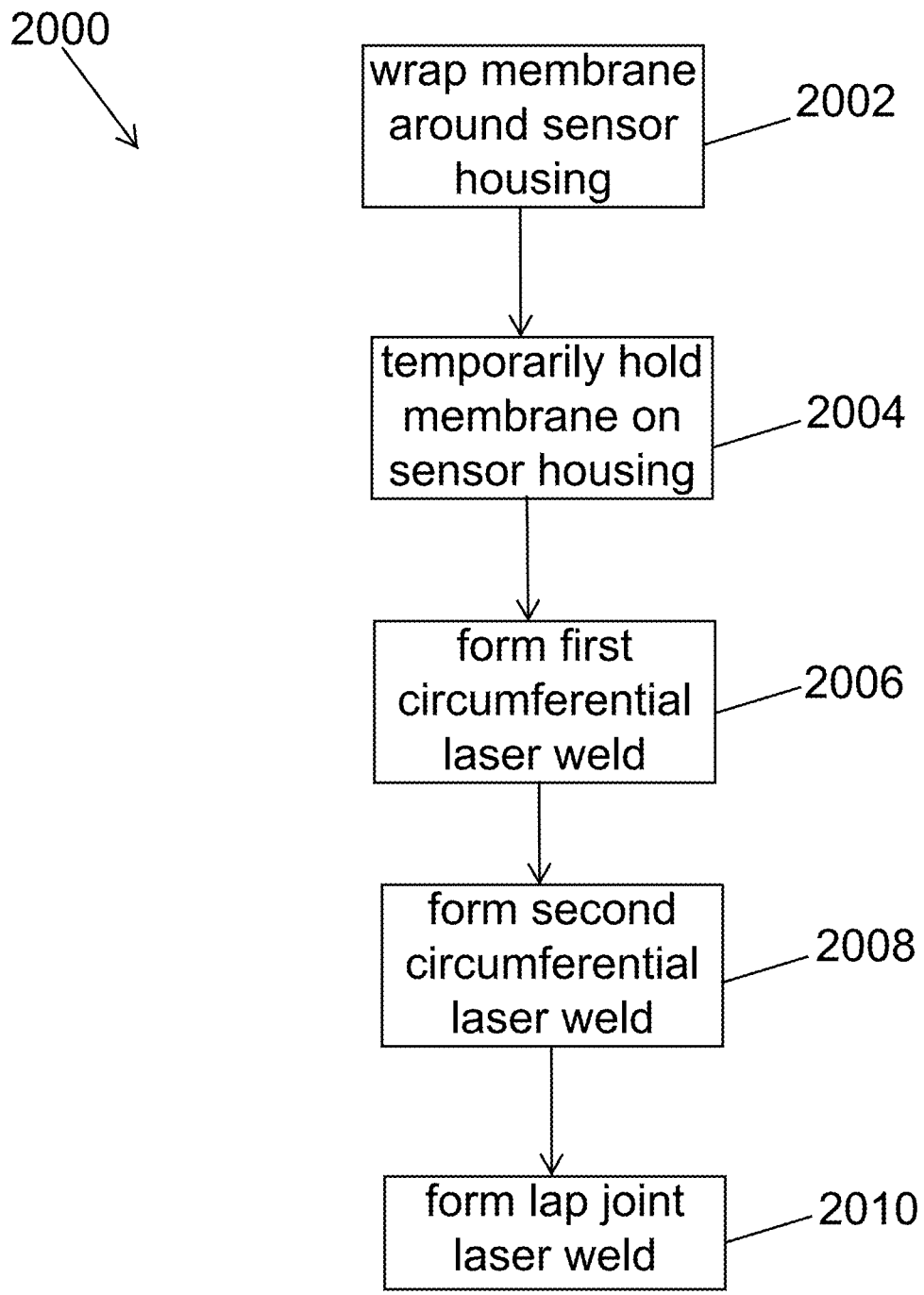
FIG. 20 is a flow chart illustrating a process for attaching a coated membrane to a sensor housing embodying aspects of the present invention.

FIG. 20 is a flow chart illustrating a process 2000 for attaching a membrane 808 to a sensor housing 102 embodying aspects of the present invention. In some embodiments, the membrane 808 may be coated with a material (e.g., platinum) configured to absorb laser light and melt. In some embodiments, the process 2000 may include a step 2002 of wrapping the membrane 808 around the sensor housing 102. In some embodiments, the process 2000 may include a step 2004 of temporarily holding the membrane 808 in place on the sensor housing 102. In some non-limiting embodiments, string (e.g., dental floss) may be used to hold the membrane 808 in place. In some non-limiting embodiments, the string may be used to hold the membrane 808 in place by one or more of using the string to form a slip knot, tightening the slip knot around the membrane 808, and wrapping the string around the membrane 808 and sensor housing 102. In some non-limiting alternative embodiments, a transparent material fixture (e.g., a glass or quartz plate) may be used to temporarily hold the membrane 808. In some non-limiting embodiments, wrapping the membrane 808 around the sensor housing 102 and temporarily holding the membrane 808 in place on the sensor housing 102 in steps 2002 and 2004 may form a lap joint (see, e.g., lap joint 2110 of FIG. 21) where two ends of the membrane 808 overlap one another.

In some embodiments, the process 2000 may include a step 2006 of forming a circumferential laser weld 1902 along an edge of the membrane 808. In some embodiments, the circumferential laser weld 1902 may be formed by irradiating the membrane 808 with laser light, which may be absorbed by the material (e.g., platinum) coated on the membrane 808 and may melt the material. In some embodiments, before the circumferential laser weld 1902 is formed, the string may be unwrapped from the edge portion of the membrane 808 where the circumferential laser weld 1902 will be formed. In some non-limiting embodiments, forming the circumferential laser weld 1902 may include forming a plurality of weld spots along the edge of the membrane 808. In some non-limiting embodiments, the first weld spot of the circumferential laser weld 1902 may be formed on the lap joint. In some alternative embodiments, forming the circumferential laser weld 1902 may include forming a continuous weld along the edge of the membrane 808. In some non-limiting embodiments, the continuous weld may begin on the lap joint. In some other alternative embodiments, forming the circumferential laser weld 1902 may include forming a zigzag line or a plurality of short lines. In some non-limiting embodiments, the first short line may be formed on the lap joint.

In some embodiments, the process 2000 may include a step 2008 of forming a circumferential laser weld 1904 along the opposite edge of the membrane 808. In some embodiments, the circumferential laser weld 1904 may be formed by irradiating the membrane 808 with laser light, which may be absorbed by the material (e.g. platinum) coated on the membrane 808 and may melt the material. In some embodiments, before the circumferential laser weld 1904 is formed, the string may be unwrapped from the edge portion of the membrane 808 where the circumferential laser weld 1904 will be formed. In some non-limiting embodiments, forming the circumferential laser weld 1904 may include forming a plurality of weld spots along the edge of the membrane 808. In some non-limiting embodiments, the first weld spot of the circumferential laser weld 1904 may be formed on the lap joint. In some alternative embodiments, forming the circumferential laser weld 1904 may include forming a continuous weld along the edge of the membrane 808. In some non-limiting embodiments, the continuous weld may begin on the lap joint. In some other alternative embodiments, forming the circumferential laser weld 1904 may include forming a zigzag line or a plurality of short lines. In some non-limiting embodiments, the first short line may be formed on the lap joint.

Although, in some embodiments, as illustrated in FIG. 20, the circumferential laser weld forming steps 2006 and 2008 may be performed after the membrane 808 is wrapped around the sensor housing 102 in step 2002 and after the membrane 808 is temporarily held on the sensor housing 102 in step 2004, this is not required. In some alternative embodiments, one or more of the circumferential laser weld forming steps 2006 and 2008 may be performed while the membrane 808 is wrapped around the sensor housing 102. For instance, in some non-limiting embodiments, a transparent material fixture may temporarily hold one end of the membrane 808 on the sensor housing 102. The sensor housing 102 may be rotated, and the transparent material fixture may press the membrane 808 against the sensor housing 102 while the sensor housing 102 is rotated. One or more of the circumferential laser welds 1902 and 1904 may be formed (e.g., by irradiating the membrane 808 with laser light that passes through the transparent material fixture before reaching the membrane 808) while the sensor housing 102 is rotated. After one complete rotation, the membrane 808 may be wrapped around the sensor housing 102 and held in place by one or more of circumferential laser welds 1902 and 1904. In some non-limiting embodiments, the sensor housing 102 may be rotated a second time to form a second circumferential laser weld (instead of forming the circumferential welds simultaneously), and, after two complete rotations, the membrane 808 may be held in place by the circumferential laser welds 1902 and 1904.

In some embodiments, the process 2000 may include a step 2010 of forming a lap joint laser weld 1906 on the lap joint where the ends of the membrane 808 overlap. In some embodiments, the lap joint laser weld 1906 may be formed by irradiating the membrane 808 with laser light, which may be absorbed by the material (e.g. platinum) coated on the membrane 808 and may melt the material. In some embodiments, before the lap joint laser weld 1906 is formed, the string may be unwrapped from the portion of the lap joint where the lap joint laser weld 1906 will be formed. In some non-limiting embodiments, forming the lap joint laser weld 1906 may include forming a plurality of weld spots along the lap joint. In some non-limiting embodiments, the first weld spot of the circumferential laser weld 1904 may be formed adjacent to one of the circumferential laser welds 1902 and 1904 at an edge of the membrane 808. In some alternative embodiments, forming the lap joint laser weld 1906 may include forming a continuous weld on the lap joint (e.g., from one edge of the membrane 808 to the other edge 808 of the membrane 808). In some non-limiting embodiments, the continuous weld may begin adjacent to one of the circumferential laser welds 1902 and 1904. In some other alternative embodiments, forming the lap joint laser weld 1906 may include forming a zigzag line or a plurality of short lines on the lap joint.

In some non-limiting embodiments, the sensor 100 may include two or more of (i) the first coating 816 on the inner surface 812 of the membrane 808, (ii) the second coating 818 on the outer surface 814 of the membrane 808, and (iii) the layer 809 on the outside of the indicator element 106, which may provide the indicator element 106 with more protection from in vivo oxidation that if only one of the first coating 816, the second coating 818, and the layer 809 were provided. In some non-limiting embodiments, the sensor 100 may include all three of (i) the first coating 816 on the inner surface 812 of the membrane 808, (ii) the second coating 818 on the outer surface 814 of the membrane 808, and (iii) the layer 809 on the outside of the indicator element 106, which may provide the indicator element 106 with more protection from in vivo oxidation that if only two of the first coating 816, second coating 818, and the layer 809 were provided. That is, including a plurality of the first coating 816, second coating 818, and the layer 809 may increase the amount of the catalyst(s) of the conversion of hydrogen peroxide into water and oxygen in the proximity of the indicator element 106, which increases protection from in vivo oxidation.

FIGS. 17A-17E illustrate non-limiting examples of sensors 100 embodying aspects of the present invention. As shown in FIG. 17A, a sensor 100 may include a sensor housing 102, an indicator element 106, and a layer 809 on the outside of the indicator element 106. As shown in FIG. 17B, a sensor 100 may include a sensor housing 102, an indicator element 106, a layer 809 on the outside of the indicator element 106, and a membrane 808. As shown in FIG. 17C, a sensor 100 may include a sensor housing 102, an indicator element 106, a layer 809 on the outside of the indicator element 106, a membrane 808, and a first coating 816 on the inner surface of the membrane 808. As shown in FIG. 17D, a sensor 100 may include a sensor housing 102, an indicator element 106, a layer 809 on the outside of the indicator element 106, a membrane 808, and a second coating 818 on the outer surface of the membrane 808 (with no first coating 816 on the inner surface of the membrane 808). As shown in FIG. 17E, a sensor 100 may include a sensor housing 102, an indicator element 106, a layer 809 on the outside of the indicator element 106, a membrane 808, a first coating 816 on the inner surface of the membrane 808, and a second coating 818 on the outer surface of the membrane 808.

Figure 17F:
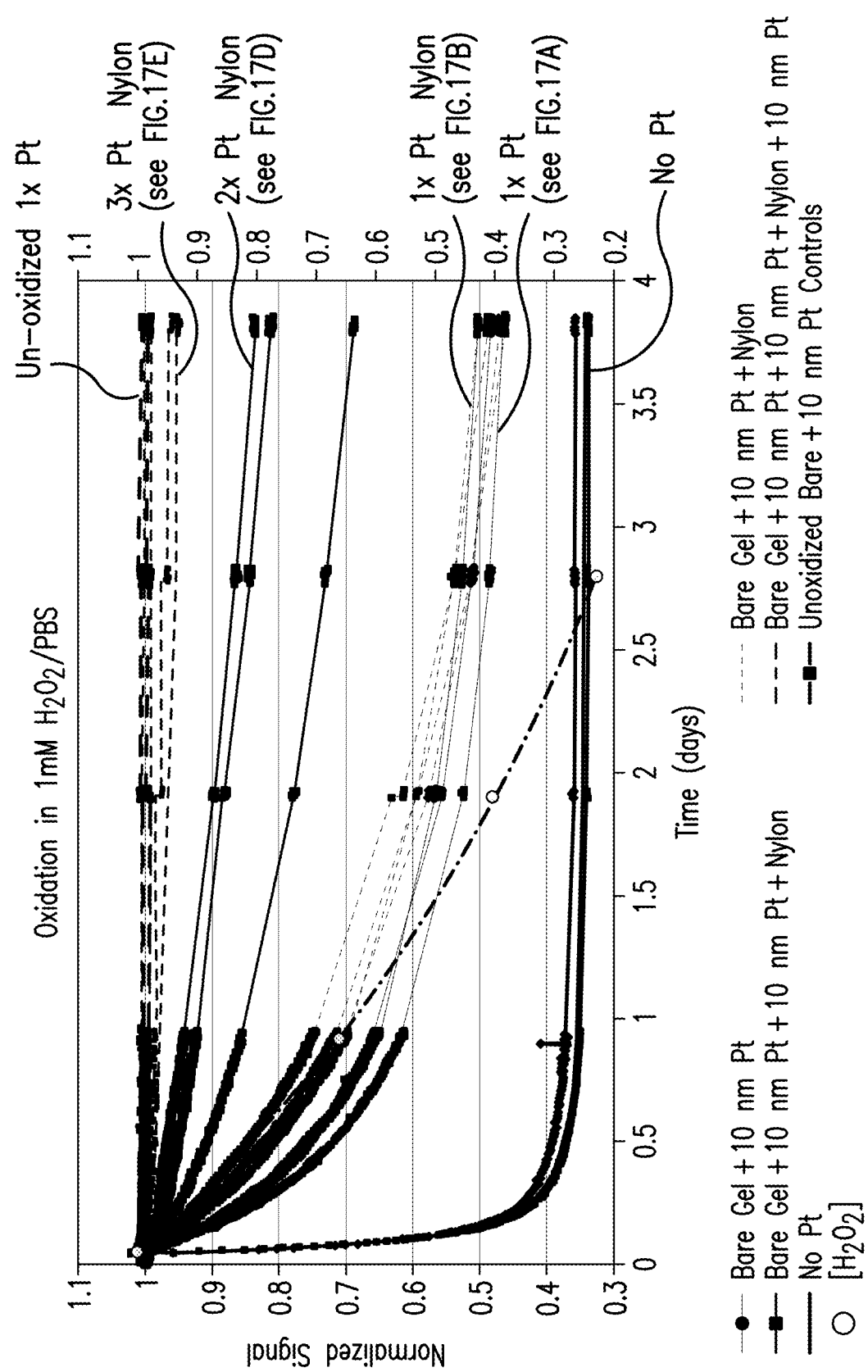
FIG. 17F is a chart illustrating the results of in vitro oxidative stability testing on the sensors illustrated in FIGS. 17A, 17B, 17D, and 17E.

FIG. 17F illustrates a non-limiting example of the results of in vitro oxidative stability testing on the examples of the sensors illustrated in FIGS. 17A, 17B, 17D, and 17E. FIG. 17F shows normalized signals (labelled "No Pt" and shown in blue) produced by sensors having no catalyst of the conversion of hydrogen peroxide into water and oxygen in the proximity of the indicator element 106. Oxidation may degrade the indicator elements 106 of these sensors and, as shown in FIG. 17F, cause the normalized signals (labelled "No Pt" and shown in blue) from the sensors to drop from 1 to less than 0.4 after only 0.5 days in a hydrogen peroxide solution.

In addition, FIG. 17F shows normalized signals (labelled "1x Pt" and shown in red) produced by sensors having a layer of platinum 809 on the outside of the indicator element 106 (and no membrane 808) (see FIG. 17A) and normalized signals (labelled "1x Pt+Nylon" and shown in green) produced by sensors having a membrane 808 made of nylon and a platinum layer 809 on the outside of the indicator element 106 (see FIG. 17B). The layer of platinum 809 reduces degradation of the indicator element 106 caused by oxidation, and, as shown in FIG. 17E, the normalized signals (labelled "1x Pt" and "1x Pt+Nylon" and shown in red and green, respectively) produced by these sensors remain above 0.5 after 2 days in the hydrogen peroxide solution.

FIG. 17F also shows normalized signals (labelled "2x Pt+Nylon" and shown in orange) produced by sensors having a membrane 808 made of nylon, a platinum coating 818 on the outer surface of the membrane 808, and a platinum layer 809 on the outside of the indicator element 106 (see FIG. 17D). The platinum coating 818 on the membrane 808 and the layer of platinum 809 reduce degradation of the indicator element 106 caused by oxidation, and, as shown in FIG. 17F, the normalized signal (labelled "2x Pt+Nylon" and shown in orange) produced by these sensors remain above 0.7 after 3 days in the hydrogen peroxide solution.

Furthermore, FIG. 17F shows normalized signals (labelled "3x Pt+Nylon" and shown in black) produced by sensors having a membrane 808 made of nylon and all three of (i) a platinum coating 816 on the inner surface of the membrane 808, (ii) a platinum coating 818 on the outer surface of the membrane 808, and (iii) a platinum layer 809 on the outside of the indicator element 106 (see FIG. 17E). The platinum coatings 816 and 818 on the membrane 808 and the layer of platinum 809 reduce degradation of the indicator element 106 caused by oxidation, and, as shown in FIG. 17F, the normalized signal (labelled "3x Pt+Nylon" and shown in black) produced by these sensors remaining above 0.9 after 4 days in the hydrogen peroxide solution.

In some embodiments, the chemical modification of the permeable membrane 808 (e.g., by coating one or more of the inner and outer surfaces of the membrane 808 with a catalyst of the conversion of hydrogen peroxide into water and oxygen) may enhance oxidative stability. In some embodiments, this configuration may result in the sensor 100 being able to last 6 months or more in vivo.

Figure 18:
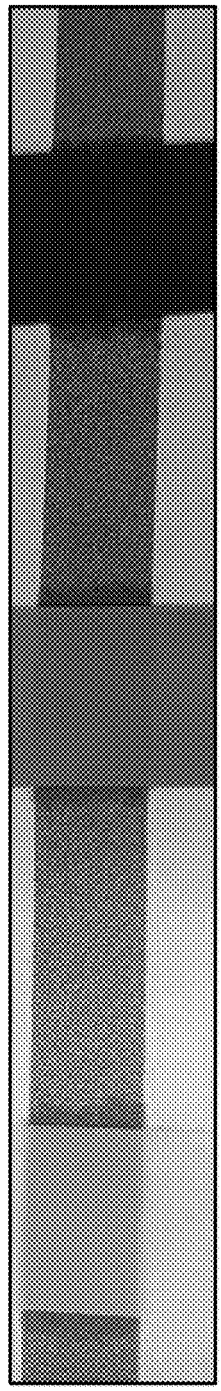
FIG. 18 shows that the visibility of a stripe through a membrane decreases when one side of the membrane is coated with platinum and decreases further when both sides of the membrane are coated with platinum.

In some embodiments, the one or more catalyst coatings on the membrane 808 may increase the light blocking capability of the membrane 808, which may reduce the amount of spurious light reaching the photodetectors of the sensor 100 and thereby improve the accuracy of the sensor 100. For example, FIG. 18 shows that the visibility of a stripe through a membrane 808 decreases when one side of the membrane 808 is coated with platinum and decreases further when both sides of the membrane 808 are coated with platinum Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, in some embodiments, the sensor 100 is a subcutaneous electro-optical sensor, but this is not required, and, in other embodiments, the sensor 100 may be a transcutaneous and/or electro-chemical sensor. Also, circuitry of the sensor 100 and reader 101 may be implemented in hardware, software, or a combination of hardware and software. The software may be implemented as computer executable instructions that, when executed by a processor, cause the processor to perform one or more functions.

For another example, although the laser bonding has been described above as attaching a membrane 808 over an indicator element 106 (and over any layer/film 809 on the outside of the indicator element 106) to a sensor housing 102, the laser bonding method is not so limited. In some alternative embodiments, the laser bonding may be used to attach other types of membranes to other objects. In some embodiments, the laser bonding may be used to attach any membrane including a material (e.g., a coating) capable of absorbing sufficient energy to create a bond between the material of the membrane and another object (e.g., a sensor housing 102 or indicator element 106). In some non-limiting alternative embodiments, the laser bonding may be used to attach one or more of an indicator membrane, a selective light filter (e.g., to prevent ambient light from passing through), a membrane having selective porosity (e.g., to filter out molecules above a certain size), a hold catalyst, and a drug elution membrane to the sensor housing 102 (and/or indicator element 106).

What is claimed is:

1. A sensor comprising:
a sensor housing;
an indicator element embedded within and/or covering at least a portion of the sensor housing;
a membrane over at least a portion of the indicator element, wherein the membrane comprises an inner surface and an outer surface;
a coating on one of the inner and outer surfaces of the membrane, wherein the coating reduces deterioration of the indicator element by catalyzing degradation of reactive oxygen species (ROS); and
a layer on the outside of the indicator element, wherein the layer is between the indicator element and the membrane and reduces deterioration of the indicator element by catalyzing degradation of ROS.

2. The sensor of claim 1, wherein the coating is on the outer surface of the membrane.

3. The sensor of claim 1, wherein the coating is on the inner surface of the membrane, and the layer is between the indicator element and the coating on the inner surface of the membrane.

4. The sensor of claim 3, wherein the coating is a first coating, the sensor further comprises a second coating on the outer surface of the membrane, and the second coating reduces deterioration of the indicator element by catalyzing degradation of ROS.

5. The sensor of claim 4, wherein the first and second coatings are sputter coatings.

6. The sensor of claim 4, wherein the first and second coatings comprise platinum.

7. The sensor of claim 1, wherein the coating is a sputter coating.

8. The sensor of claim 1, wherein the coating comprises platinum.

9. The sensor of claim 1, wherein the layer comprises platinum.

10. The sensor of claim 1, wherein the layer is sputtered on the outside of the indicator element.

11. The sensor of claim 1, wherein the membrane with the coating on one of the inner and outer surfaces of the membrane is opaque.

12. The sensor of claim 1, wherein the membrane is attached to the sensor housing.

13. The sensor of claim 12, wherein the membrane is attached to the sensor housing by heat bonding or with a biocompatible adhesive.

14. The sensor of claim 12, wherein the membrane is attached to the sensor housing using laser bonding.

15. The sensor of claim 1, wherein the membrane is a mesh material.

16. The sensor of claim 1, wherein the membrane has pores configured to substantially prevent white blood cells from passing through the membrane but to permit the analyte to pass through the membrane.

17. The sensor of claim 16, wherein the analyte is glucose.

18. The sensor of claim 1, wherein the membrane is wrapped around the indicator element.

19. The sensor of claim 1, wherein the indicator element is a polymer graft including indicator molecules.

20. The sensor of claim 1, wherein one or more of the membrane and the coating are configured to block (i) external light from reaching the indicator element and (ii)

light from the sensor housing that has passed through the indicator element from reaching the bodily tissue of the living animal.

* * * * *